(12) United States Patent
Cooymans et al.

(10) Patent No.: US 9,896,459 B2
(45) Date of Patent: Feb. 20, 2018

(54) AZAINDOLES AS RESPIRATORY SYNCYTIAL VIRUS ANTIVIRAL AGENTS

(71) Applicant: Janssen Sciences Ireland UC, Co Cork (IE)

(72) Inventors: Ludwig Paul Cooymans, Beerse (BE); Samuël Dominique Demin, Antwerp (BE); Lili Hu, Mechelen (BE); Tim Hugo Maria Jonckers, Edegem (BE); Pierre Jean-Marie Bernard Raboisson, Rosieres (BE); Abdellah Tahri, Anderlecht (BE); Sandrine Marie Helene Vendeville, Woluwe-Saint-Pierre (BE)

(73) Assignee: Janssen Sciences Ireland UC, Co Cork (IE)

( * ) Notice: Subject to any disclaimer, the term of this patent is extended or adjusted under 35 U.S.C. 154(b) by 0 days.

(21) Appl. No.: 15/153,591

(22) Filed: May 12, 2016

(65) Prior Publication Data

US 2016/0251377 A1  Sep. 1, 2016

Related U.S. Application Data

(60) Continuation of application No. 14/704,292, filed on May 5, 2015, now Pat. No. 9,339,494, which is a division of application No. 13/993,543, filed as application No. PCT/EP2011/073016 on Dec. 16, 2011, now Pat. No. 9,051,317.

(30) Foreign Application Priority Data

Dec. 16, 2010 (EP) .................................. 10195473

(51) Int. Cl.
C07D 519/00 (2006.01)
C07D 471/04 (2006.01)
A61K 31/437 (2006.01)

(52) U.S. Cl.
CPC .......... *C07D 519/00* (2013.01); *A61K 31/437* (2013.01); *C07D 471/04* (2013.01)

(58) Field of Classification Search
CPC ... C07D 519/00; C07D 471/04; A61K 31/437
USPC ....................................................... 546/118
See application file for complete search history.

(56) References Cited

U.S. PATENT DOCUMENTS

| | | | |
|---|---|---|---|
| 6,489,338 B2 | 12/2002 | Gulgeze et al. | |
| 6,506,738 B1 | 1/2003 | Yu et al. | |
| 6,534,535 B1 | 3/2003 | Zhu et al. | |
| 6,919,331 B2 | 7/2005 | Yu et al. | |
| 7,361,657 B2 | 4/2008 | Janssens et al. | |
| 7,528,149 B2 | 5/2009 | Janssens et al. | |
| 8,846,672 B2* | 9/2014 | Cooymans | C07D 487/04 514/233.2 |
| 8,865,705 B2* | 10/2014 | Cooymans | C07D 471/04 514/222.2 |
| 8,921,560 B2* | 12/2014 | Cooymans | C07D 403/06 546/113 |
| 8,927,720 B2* | 1/2015 | Cooymans | C07D 471/04 546/117 |
| 9,051,317 B2* | 6/2015 | Cooymans | A61K 31/437 |
| 9,321,767 B2* | 4/2016 | Cooymans | C07D 471/04 |
| 9,321,768 B2* | 4/2016 | Cooymans | C07D 403/06 |
| 9,339,494 B2* | 5/2016 | Cooymans | C07D 471/04 |
| 2002/0016309 A1 | 2/2002 | Yu et al. | |
| 2004/0166137 A1 | 8/2004 | Lackey | |
| 2011/0009444 A1 | 1/2011 | Dubois et al. | |
| 2013/0261151 A1 | 10/2013 | Cooymans et al. | |
| 2013/0267508 A1 | 10/2013 | Cooymans et al. | |
| 2013/0267555 A1 | 10/2013 | Cooymans et al. | |
| 2013/0267556 A1 | 10/2013 | Cooymans et al. | |
| 2013/0324527 A1 | 12/2013 | Cooymans et al. | |
| 2015/0073012 A1* | 3/2015 | Cooymans | C07D 471/04 514/303 |
| 2015/0073013 A1* | 3/2015 | Cooymans | C07D 403/06 514/303 |

(Continued)

FOREIGN PATENT DOCUMENTS

FR  2926556  7/2009
JP  2008522968  6/2006

(Continued)

OTHER PUBLICATIONS

Banker, et al., Modern Pharmaceutics, 3 edition, 1996, pp. 451 and 596.

(Continued)

*Primary Examiner* — Daniel R Carcanague

(57) ABSTRACT

Azaindoles having inhibitory activity on RSV replication and having the formula I

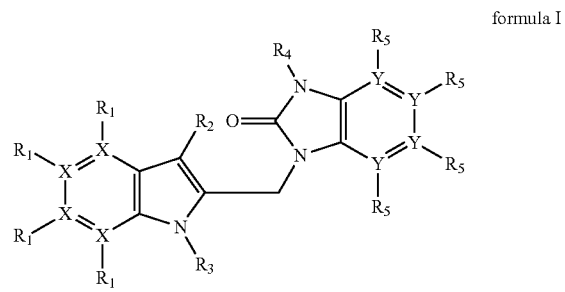

compositions containing these compounds as active ingredient and processes for preparing these compounds and compositions.

3 Claims, No Drawings

(56) References Cited

U.S. PATENT DOCUMENTS

| | | | |
|---|---|---|---|
| 2015/0111868 A1* | 4/2015 | Tahri | C07D 403/14 514/210.18 |
| 2015/0158862 A1* | 6/2015 | Tahri | C07D 471/04 514/303 |
| 2015/0166533 A1* | 6/2015 | Tahri | C07D 471/04 514/210.18 |
| 2015/0175608 A1* | 6/2015 | Tahri | C07D 235/20 514/303 |
| 2015/0231119 A1* | 8/2015 | Cooymans | A61K 31/437 514/303 |
| 2015/0259367 A1* | 9/2015 | Tahri | C07D 403/06 514/210.21 |
| 2016/0122346 A1* | 5/2016 | Tahri | C07D 403/14 514/210.18 |
| 2016/0237083 A1 | 8/2016 | Cooymans et al. | |
| 2016/0237096 A1* | 8/2016 | Cooymans | C07D 471/04 |
| 2016/0251377 A1 | 9/2016 | Cooymans et al. | |

FOREIGN PATENT DOCUMENTS

| | | |
|---|---|---|
| WO | WO98/01428 | 1/1998 |
| WO | WO00/20400 | 4/2000 |
| WO | WO00/35886 A | 6/2000 |
| WO | 2001057019 A1 | 8/2001 |
| WO | WO01/47020 A | 8/2001 |
| WO | WO01/95910 | 12/2001 |
| WO | WO02/26228 | 1/2002 |
| WO | WO03/053344 | 4/2003 |
| WO | 2003049688 A2 | 6/2003 |
| WO | 2003056344 A2 | 7/2003 |
| WO | 2004069256 A1 | 8/2004 |
| WO | 2006062465 A1 | 6/2006 |
| WO | WO2006/062465 A | 6/2006 |
| WO | 2008147697 A1 | 12/2008 |
| WO | 2012080446 A1 | 6/2012 |
| WO | 2012080447 | 6/2012 |
| WO | 2012080449 A1 | 6/2012 |
| WO | 2012080450 A1 | 6/2012 |
| WO | 2012080481 A1 | 6/2012 |
| WO | WO2012080451 | 6/2012 |
| WO | 2013186335 A1 | 12/2013 |
| WO | WO2013186332 | * 12/2013 |
| WO | WO2013186333 | * 12/2013 |
| WO | WO2013186334 | * 12/2013 |

OTHER PUBLICATIONS

Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.

Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.

Wolff, et al., "Burger's Medicinal Chemistry, 5th edition", Part I, 1997, pp. 975-977.

Wermuth, "Molecular Variations Based on Isosteric Replacements", Practice of Medicinal Chemistry 3rd edition, 2008, pp. 290-342.

Yu et al., "Respiratory Syncytial Virus Fusion Inhibitors. Part 4: Optimization for Oral Bioavailability" Biorganic & Medicinal Chemistry letters, vol. 17, 2007, pp. 895-901.

Silverman, et al., The Organic of Drug Design and Drug Action, 2004, pp. 29-34.

Goodman, et al, Biotransformation of Drugs:, The Pharmacological Basis of Therapeutics, 8th ed., 1992, pp. 13-15.

Giampieri, et al., "Antiviral Activity of Indole Derivatives", Antiviral Research, vol. 83, 2009, pp. 179-185.

Wyde, et al., AWY Dentiviral Research, vol. 38, 1998, pp. 31-42.

Pearce, et al., "E-Novo: An Automated Workflow for efficient Structure-Based Lead Optimization" J. Chem. Inf. Model, 2009, vol. 49, pp. 1797-1809.

Ito, et al., "A Medium-Term Rat Liver Bioassay for Rapid in Vivo Detection of Carcinogenic Potential of Chemicals" Cancer Science, 94(1) 2003, pp. 3-8.

Database Registry Chemical Abstracts Service, Columbus, Ohio, Assession No. RN 941045-14-3 and RN 931665-23-5.Entered STN: Jul. 4, 2007 and Apr. 22, 2007.

Hallak et al, "Glycosaminoglycan Sulfation Requirements for Respiratory Syncytial Virus Infection", Journal of Virology, vol. 74, No. 22 (Nov. 2000), pp. 10508-10513.

Tonelli et al, "Antiviral Activity of Benzimidazole Derivaties. I. Antiviral Activity of 1-Substituted-2-[(Benzotriazol-1/2-yl)methyl]benzimidazoles)", Chemistry & Biodiversity, vol. 5 (2008) pp. 2386-2401.

Yu, et al., "Respiratory Syncytial Virus Inhibitors. Part 2: Benzimidazole-2-one Derivatives", Bioorganic & Medicinal Chemistry Letters 14 (2004) pp. 1133-1137.

Mackman; J. Med. Chem. 2015, 58, 1630-1643.

International Search Report—PCT/EP2011/073008, dated, Mar. 28, 2012.

International Search Report—PCT/EP2011/073011, dated, Mar. 27, 2012.

International Search Report—PCT/EP2011/073014, dated Mar. 28, 2012.

International Search Report—PCT/EP2011/073016, dated Mar. 27, 2012.

International Search Report—PCT/EP2011/073017, dated Mar. 28, 2012.

Goodman, et al, "Desymmetrization of Dichloroazaheterocycles", Tetrahedron, vol. 55: pp. 15067-15070 (1999).

Greene, et al., "Protection for the Hydroxyl Group Including 1,2- and 1,3-diols." Protective Groups in Organic Synthesis, 3rd edition, pp. 119-121 (1999). XP002670712.

Negishi, "3 Fluorine as an Organic Compound", Flourine Chemistry Towards New Functionality, pp. 89-90 (Jun. 30, 1988).

Nozaki, et al., "Chapter 5: Structure-Activity Relationship and Drug Design", Medicinal Chemistry, pp. 98-99 (Jul. 1, 1995).

Provencal, et al, "Development of an Efficient and Scalable Process of Respiratory Syncytial Virus Inhibitor", Organic Process Research & Development, 2004, pp. 903-908, vol. 8.

Qidong, et al., Pharmaceutical Chemistry, Chemical Industry Press, Jan. 2004, pp. 32-34, 2004.

Venkatesh, et al., "Role of the Development Scientist in Compound Lead to Selection and Optimization", Journal of Pharmaceutical Sciences, Feb. 2000, pp. 145-154, vol. 89 (2).

Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).

Wermuth (Editor), "The Latest Medicinal Chemistry: Chapter 13—Molecular Variations based on Isosteric Replacement", The Latest Medicinal Chemistry, 1998, pp. 235-271, vol. 1.

Wermuth (Editor), "The Practice of Medicial Chemistry", The Lastest Medicinal Chemistry, 1993, pp. 375-380, vol. 1.

Wermuth, (Editor), The Practice of Medicinal Chemistry, Designing Prodrugs and Bioprecursors I: Carrier Prodrugs, 1996, pp. 672-696, vol. 31, Academic Press Limited.

West, A.R., "Chapter 10 Solid Solutions", Solid State Chemistry and Its Applications, John Wiley & Sons, pp. 33-36 (1984).

Wolff, et al, Burger's Medicinal Chemistry and Drug Discovery,—, 1994, pp. 975-977, 5th Edition, vol. 1.

Yamanaka (Editor), "Introduction to Fluorine Chemistry: The Role of Fluorine Chemistry in Cutty Edge Technology", Japan Society for the Promotion of Science, 2005, pp. 398-403.

International Search Report for Corresponding Application No. PCT/EP2013/062321, dated Jul. 16, 2013.

International Search Report for Corresponding Application No. PCT/EP2013/062322, dated Aug. 21, 2013.

International Search Report for Corresponding Application No. PCT/EP2013/062324, dated Jul. 18, 2013.

International Search Report for Corresponding Application No. PCT/EP2013/062325, dated Jul. 17, 2013.

* cited by examiner

AZAINDOLES AS RESPIRATORY SYNCYTIAL VIRUS ANTIVIRAL AGENTS

CROSS REFERENCE TO RELATED APPLICATIONS

This application is a continuation of U.S. application Ser. No. 14/704,292, filed May 5, 2015, now U.S. Pat. No. 9,339,494, which is a divisional of U.S. application Ser. No. 13/993,543, filed Jun. 12, 2013, now U.S. Pat. No. 9,051,317, which is the national stage entry under 35 U.S.C. 371 of PCT Application No. PCT/EP2011/073016, filed Dec. 16, 2011, which application claims priority from European Patent Application No. EP 10195473.3, filed Dec. 16, 2010 the entire disclosures of which are hereby incorporated by reference in their entirety.

FIELD OF THE INVENTION

The invention concerns azaindoles having antiviral activity, in particular, having an inhibitory activity on the replication of the respiratory syncytial virus (RSV). The invention further concerns the preparation of these azaindoles, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference entitles "imidazopyridine and imidazopyrimidine antiviral agents" is WO 01/95910 which, in fact, relates to benzimidazole antiviral agents. Herein compounds are presented to have antiviral activity, yet with $EC_{50}$ values over a wide range of from 0.001 μm to as high as 50 μM (which does not normally represent the desired biological activity). Another reference, relating to substituted 2-methyl-benzimidazole RSV antiviral agents, in the same range of activities is WO 03/053344. Another related background reference of compounds in the same range of activities, is WO 02/26228 regarding benzimidazolone antiviral agents. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 5004), and preferably at a level of about the most active, more preferably of even stronger activity, than the compounds disclosed in the art. A further desire is to find compounds having oral antiviral activity.

SUMMARY OF THE INVENTION

In order to better address one or more of the foregoing desires, the invention, in one aspect, presents antiviral azaindole compounds represented by formula I, a prodrug, N-oxide, addition salt, quaternary amine, metal complex, or a stereochemically isomeric form thereof;

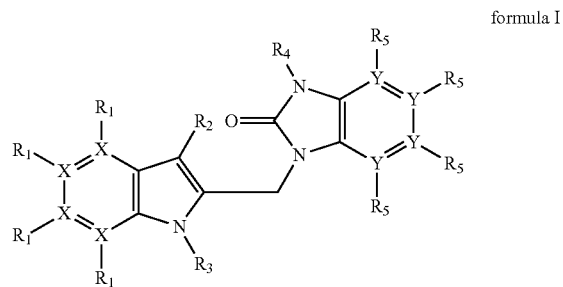

formula I wherein each X independently is C or N with at least one X being N;

$R_1$ is present where X═C and $R_1$ selected from the group of H, OH, halogen, $C_1$-$C_6$alkyl, $C_3$-$C_7$cycloalkyl, $C_1$-$C_6$alkoxy, N($R_6$)$_2$, CO($R_7$), CH$_2$NH$_2$, CH$_2$OH, CN, C(═NOH)NH$_2$, C(═NOCH$_3$)NH$_2$, C(═NH)NH$_2$, CF$_3$, OCF$_3$, and B(OH)$_2$; B(O—$C_1$-$C_6$alkyl)$_2$;

$R_2$ is selected from the group consisting of H, halogen, $C_1$-$C_6$alkyl, $C_3$-$C_7$cycloalkyl, $C_1$-$C_6$alkoxy, and CO($R_7$);

$R_3$ is —(CR$_8$R$_9$)$_n$—R$_{10}$;

$R_4$ is selected from the group consisting of H, $C_1$-$C_{10}$alkyl, $C_3$-$C_7$cycloalkyl, $C_2$-$C_{10}$alkenyl, SO$_2$—R$_8$, CH$_2$CF$_3$, or a 4 to 6 membered saturated ring containing an oxygen atom;

$R_5$ is present where Y is C, and is selected from the group consisting of H, $C_1$-$C_6$alkyl, $C_3$-$C_7$cycloalkyl, $C_1$-$C_6$alkoxy, CO($R_7$), CF$_3$ and halogen;

$R_5$ is absent where X is N;

$R_6$ is selected from the group consisting of H, $C_1$-$C_6$alkyl, $COOCH_3$, and $CONHSO_2CH_3$;

$R_7$ is selected from the group consisting of OH, O($C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl), and $N(C_1$-$C_6$-alkyl)$_2$;

n is an integer from 2 to 6;

$R_8$ and $R_9$ are each independently chosen from H, $C_1$-$C_{10}$alkyl, $C_3$-$C_7$cycloalkyl or $R_8$ and $R_9$ taken together form a 4 to 6 membered aliphatic ring that optionally contains a heteroatom selected from the group N, S, O;

$R_{10}$ is selected from the group consisting of H, $C_1$-$C_6$alkyl, OH, CN, F, $CF_2H$, $CF_3$, $CONR_8R_9$, $COOR_8$, $CONR_8SO_2R_9$, $CON(R_8)SO_2N(R_8R_9)$, $NR_8R_9$, $NR_8COOR_9$, $OCOR_8$, $NR_8SO_2R_9$, $SO_2NR_8R_9$, $SO_2R_8$ or a 4 to 6 membered saturated ring containing an oxygen atom.

In a preferred embodiment, $R_1$ is present where X is C and $R_1$ selected from the group of H, halogen, $C_1$-$C_6$alkyl, $C_3$-$C_7$cycloalkyl, $C_1$-$C_6$alkoxy, $N(R_6)_2$, $CO(R_7)$, $CH_2NH_2$, $CH_2OH$, CN, C(=NOH)$NH_2$, C(=NOCH$_3$)$NH_2$, C(=NH)$NH_2$, $CF_3$, $OCF_3$, and $B(OH)_2$; $B(O-C_1$-$C_6$alkyl)$_2$;

In another embodiment, the invention relates the compound according to formula 1 wherein $R_4$ is selected from the group consisting of H, $C_1$-$C_{10}$alkyl, $C_3$-$C_7$cycloalkyl, $C_2$-$C_{10}$alkenyl, $SO_2$—$R_8$, or a 4 to 6 membered saturated ring containing an oxygen atom.

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The molecules of formula I, in deviation from the prior art, have on one side (the left side in the formula as depicted) a substituted azaindole moiety. The invention, in a broad sense, is based on the judicious recognition that these substituted azaindole compounds generally possess an interesting RSV inhibitory activity. Moreover, these compounds enable access to anti-RSV activities at the higher regions (i.e. the lower end of the $EC_{50}$ values) of the range available in the aforementioned references. Particularly, on the basis of these compounds, molecular structures can be uncovered that even outperform the reference compounds in terms of biological activities.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

As used herein $C_{1-6}$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_{1-10}$alkyl as a group or part of a group defines straight or branched chain saturated hydrocarbon radicals having from 1 to 10 carbon atoms such as the groups defined for $C_{1-6}$alkyl and heptyl, octyl, nonyl, 2-methylhexyl, 2-methylheptyl, decyl, 2-methylnonyl, and the like;

The term '$C_2$-$C_{10}$alkenyl' used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like;

Whenever a $C_2$-$C_{10}$alkenyl group is linked to a heteroatom it preferably is linked via a saturated carbon atom.

$C_1$-$C_6$-alkoxy, as a group or part of a group defines an O—$C_1$-$C_6$alkyl radical, wherein $C_1$-$C_6$alkyl has, independently, the meaning given above.

$C_3$-$C_7$cycloalkyl is generic to cyclopropyl, cyclobutyl, cyclopentyl, cyclohexyl or cycloheptyl.

The term —$(CR_8R_9)_n$ used herein defines n repetitions of the $CR_8R_9$ subgroup, wherein each of these subgroups is independently defined.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

It will be appreciated that the compounds of the invention, with reference to the aforementioned left- and right-hand parts of formula I, present a wide variety of modification.

Without detracting from the overall scope of the invention, certain embodiments are discussed in more detail below.

In a preferred embodiment at most two X are N. In a preferred embodiment, one X is N. In a more preferred embodiment, the one X that is N is in meta or para position to N—$R_3$. In a further preferred embodiment, X is in the position para to N—$R_3$.

In one preferred embodiment, $R_1$ is selected from the group consisting of H or halogen. In a further preferred embodiment, $R_1$ in the para position to N—$R_3$ is halogen, and all other $R_1$ are H. In a further preferred embodiment halogen is bromo or chloro. In a most preferred embodiment, halogen is chloro.

In another preferred embodiment, $R_3$ comprises a —$(CR_8R_9)_n$— chain wherein $R_8$ and $R_9$ are preferably H and n is 2-4. Preferably $R_{10}$ is selected from the group consisting of OH, F, $CF_3$, $CF_2H$ and $C_1$-$C_6$alkyl, more preferably 2-propyl.

In a preferred embodiment $R_4$ is $C_3$-$C_7$cycloalkyl, more preferably cyclopropyl or oxetan-3-yl In a preferred embodiment, and more preferably in conjunction with the other preferred embodiments, one Y is N, and the other Y's are C. In a most preferred embodiment, the one Y that is N, is the Y in para position to N—$R_4$.

Preferably at most one $R_5$ is selected from the group consisting of $C_1$-$C_6$ alkyl, $C_1$-$C_6$alkoxy, halogen. More preferably $R_5$ is fluoro. Most preferably, all $R_5$ are H.

Preferred compounds are the compounds listed in table 1 and 2 below. More preferred are compounds number P1, P2, P3, P4, P5, and P6. Most preferred are compounds P1, P2, and P3. An additional preferred compound is P11.

The compounds of formula I may be prepared by the methods described below, using synthetic methods known in the art of organic chemistry, or modifications and derivatisations that are familiar to those of skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

The following schemes are exemplary of the processes for making compounds of formula I. In the schemes below, the numerals used, including numerals from I to XVII, are used for convenience to designate the formulae in the schemes. The use of numerals from I to XVII in the schemes below is not intended to imply that the compounds designated by such numerals correspond to the compounds of formulae I to XVII that are disclosed herein above and that are recited in the appended claims.

Scheme 1: General synthesis of compounds of formula I

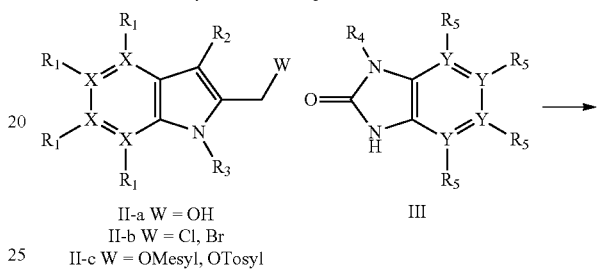

II-a W = OH
II-b W = Cl, Br
II-c W = OMesyl, OTosyl

III

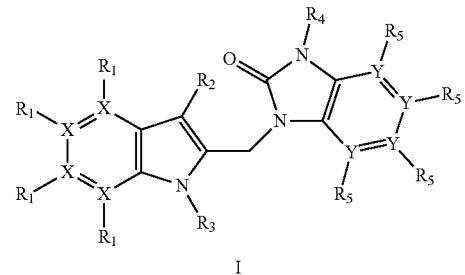

I

Scheme 1 illustrates a method for the preparation of compounds of formula I, where $R_1$ to $R_5$, X and Y are defined as above.

A compound of formula I can be synthesized by coupling 2-hydroxymethylene indole II-a with a benzimidazolone III in a known in the art method such as Mitsunobu reaction which uses azadiisopropyldicarboxylate (DIAD) and triphenylphosphine in a suitable solvent such as DMF or THF. Alternatively, compounds of formula I may be prepared by displacement of W, which is a halide, preferably chlorine II-b, or sulfonate such as mesylate II-c in the presence of a base such as, but not limiting to, sodium hydride, potassium carbonate or cesium carbonate in a suitable solvent such as DMF or THF.

Scheme 2: General synthesis of II-a type compounds

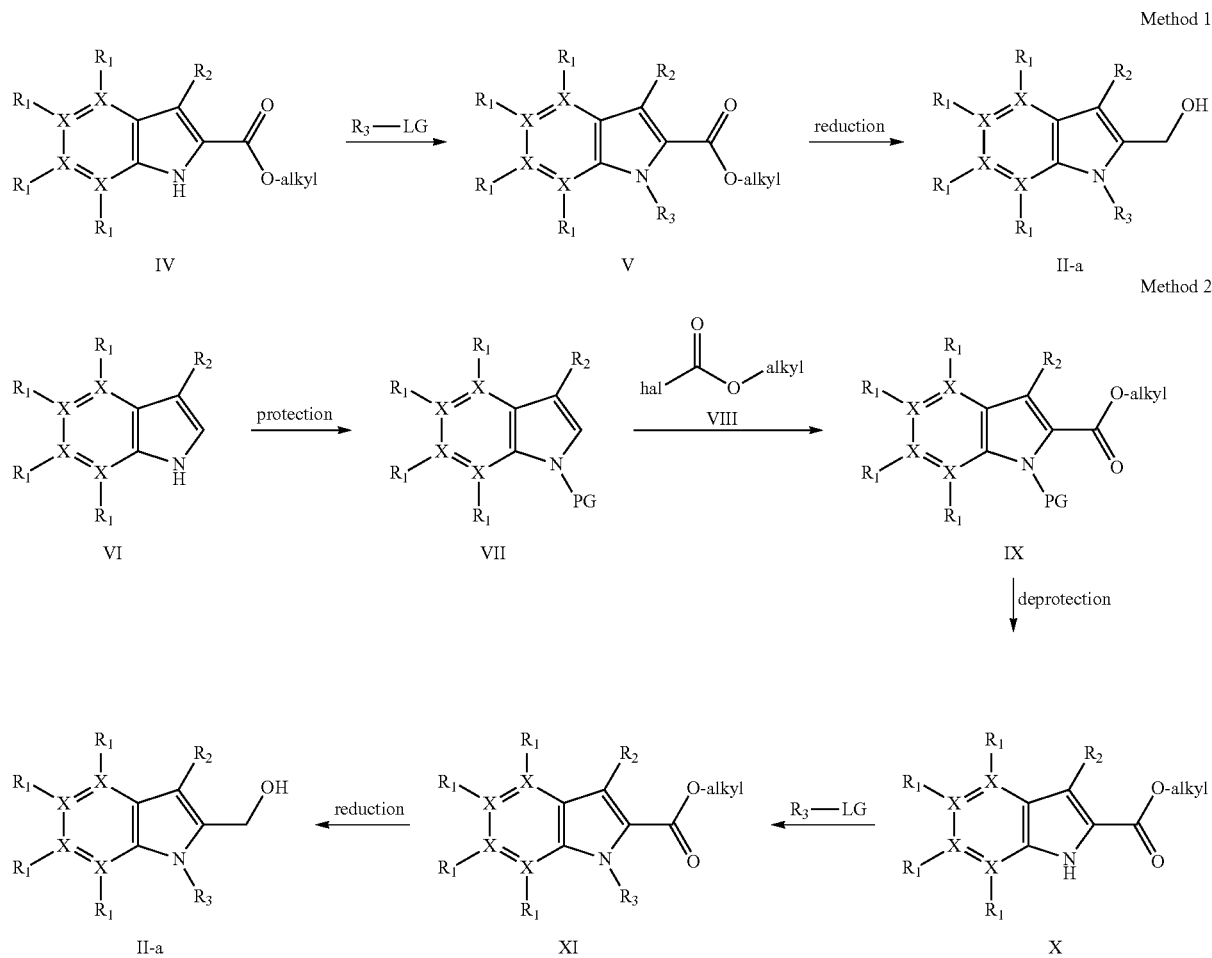

Compound II-a is prepared according to the methods as depicted in scheme 2.

Starting materials IV used in this invention, according to method 1, are commercially available, or can be synthesized, but not limited to, by methods known in the art such as Reissert synthesis or Fischer synthesis. Reaction of such a compound with $R_3$-LG, where LG is a leaving group such as halide, preferably bromine, or sulfonate, in the presence of a base such as sodium hydride, potassium carbonate or cesium carbonate in a suitable solvent such as DMF or THF, gives compound V. The conversion of the alkyl ester of compound V to the alcohol II-a can be done with a metal hydride such as lithium aluminum hydride or sodium borohydride in a suitable solvent such as THF or methanol.

Alternatively a II-a type compound can also be synthesized as shown in scheme 2, method 2. The commercially available starting material VI is protected by a PG, where PG is a protecting group such as, but not limiting to, a tosyl, which consequently results in compound VII. A suitable solvent for this kind of reactions can be, but not limiting to, toluene. The metallation of compound VII followed by treatment with compound VIII, wherein the halide is preferably chlorine, in a suitable solvent such as, but not limited to, THF, yields compound IX. The removal of the PG in compound IX may be done in the presence of a base such as potassium carbonate or cesium carbonate in a suitable solvent such as THF and methanol to obtain indole X. Reaction of indoles X with $R_3$-LG, where LG is a leaving group such as a halide, preferably bromine, or sulfonate, in the presence of a base such as sodium hydride, potassium carbonate or cesium carbonate in a suitable solvent such as DMF or THF, gives compound XI. The conversion of the alkyl ester of compound XI to the alcohol II-a can be carried out with a metal hydride such as lithium aluminum hydride or sodium borohydride in a suitable solvent such as THF or ethanol.

Scheme 3: General synthesis of II-b and II-c type compounds

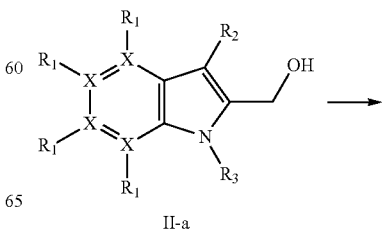

-continued

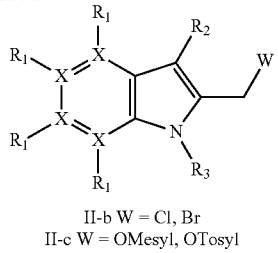

II-b W = Cl, Br
II-c W = OMesyl, OTosyl

Treatment of the alcohol II-a with reagents like, but not limiting to, $SOCl_2$, $PBr_3$, p-TsCl, MsCl provides 2-chloromethyl indole II-b or compounds like II-c.

Scheme 4: General synthesis of III type compounds

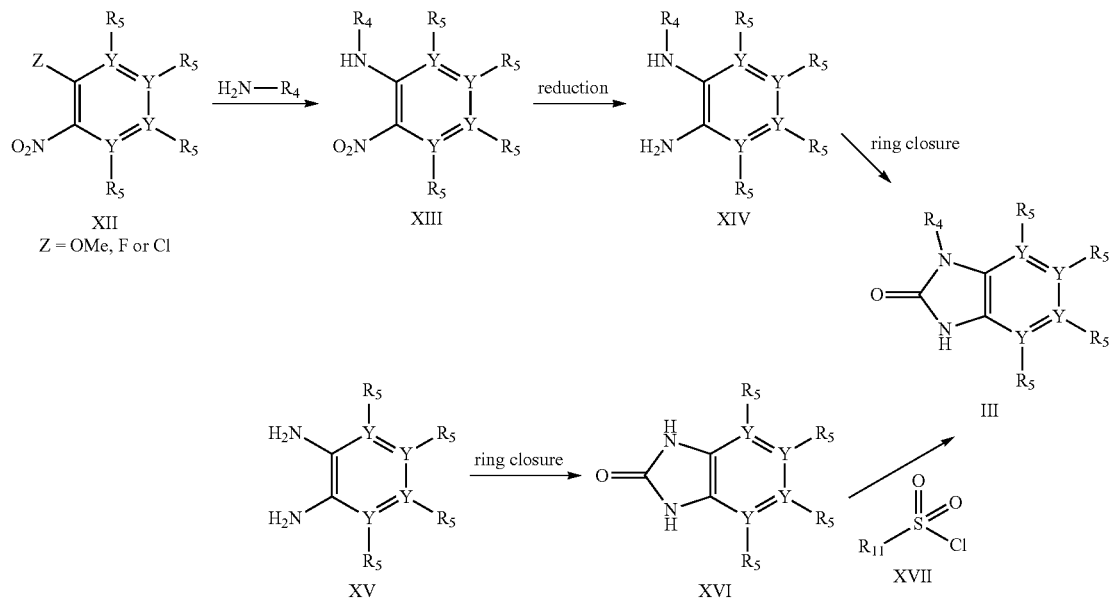

Compounds III can be synthesized using the procedure depicted in scheme 4.

Displacement of Z, which is a halide, preferably fluorine, or an alkoxy group, preferably methoxy, of XII with an amine $H_2N$—$R_4$, in a suitable solvent such as THF or DMF, in the presence of an organic base such as triethylamine or diisopropylethylamine, gives compounds XIII. Reduction of the nitro group to the amine XIV can be done in a catalytic way using hydrogen in the presence of a catalyst such as palladium or platinum, in a suitable solvent such as methanol, or in a stoichiometric way using iron in the presence of ammoniumchloride or tin chloride in the presence of concentrated hydrochloric acid. The cyclisation of the resulting diamine XIV using CDI, phosgene or triphosgene, in a solvent such as acetonitril or THF, provides III.

Alternatively, compound of type III may be prepared starting from commercially available dianilines XV which can be cyclized by ring closure with CDI, phosgene or triphosgene yielding intermediates of type XVI. Alkylation or of the urea nitrogen of XVI can be accomplished by a Mitsunobu reaction with commercially available alcohols, or by displacement of the chlorine in the compounds of type XVII to yield compound of formula III. Sulfonylation of the urea nitrogen of XVI can be accomplished by reaction of XVI type compounds with a sulphonylchloride of XVII.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I)

involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the embodiments of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the embodiments of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the embodiments of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Example 1

A detailed description of the synthesis of a representative example of the invention, compound P1 is given below.

Scheme 5: Synthesis of 1-cyclopropyl-1H-imidazo[4,5-c]pyridin-2(3H)-one (5-d)

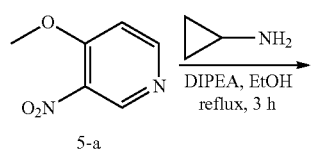

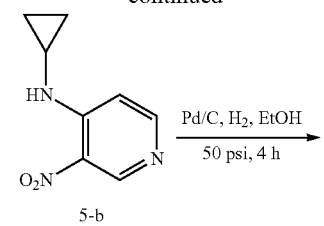

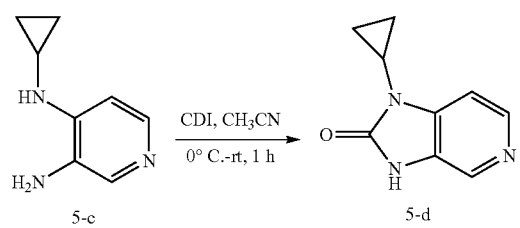

Step 1: Synthesis of N-cyclopropyl-3-nitropyridin-4-amine (5-b)

4-Methoxy-3-nitropyridine 5-a (CAS 31872-62-5) (200 g, 1300 mmol), cyclopropyl-amine (CAS 765-30-0) (185.5 g, 3250 mmol) and DIEA (CAS 7087-68-5) (336 g, 2600 mmol) in dry ethanol (800 mL) was refluxed for 3 hours. The mixture was cooled to 0° C. The solid was collected by filtration. The filter cake was washed with cold ethanol (150 mL). The solid was dried to afford compound 5-b as a white powder (167 g, 72%).

Step 2: Synthesis of N⁴-cyclopropylpyridine-3,4-diamine (5-c)

A mixture of the intermediate 5-b (167 g, 932 mmol) in ethanol (1400 mL) was hydrogenated (50 Psi) at 20° C. with wet 10% Pd/C (34 g) as a catalyst overnight. After uptake of H$_2$ (3 eq.), the catalyst was filtered off and the filtrate was evaporated. The residue was washed with MTBE to afford compound 5-c as a yellow powder (133 g, 95%).

Step 3: Synthesis of 1-cyclopropyl-1H-imidazo[4,5-c]pyridin-2(3H)-one (5-d)

CDI (CAS 530-62-1) (151.8 g, 936 mmol) was added to a solution of the intermediate 5-c (133 g, 891.4 mmol) in CH$_3$CN (1800 mL) at 0° C. The reaction was allowed to warm to 10° C. and stirred for 1 hour. The solid was collected by filtration, then washed with CH$_3$CN (200 mL) to afford compound 5-d as a white powder (101 g, 65%).

Scheme 6: Synthesis of methyl 1H-pyrrolo[3,2-c]pyridine-2-carboxylate (6-d)

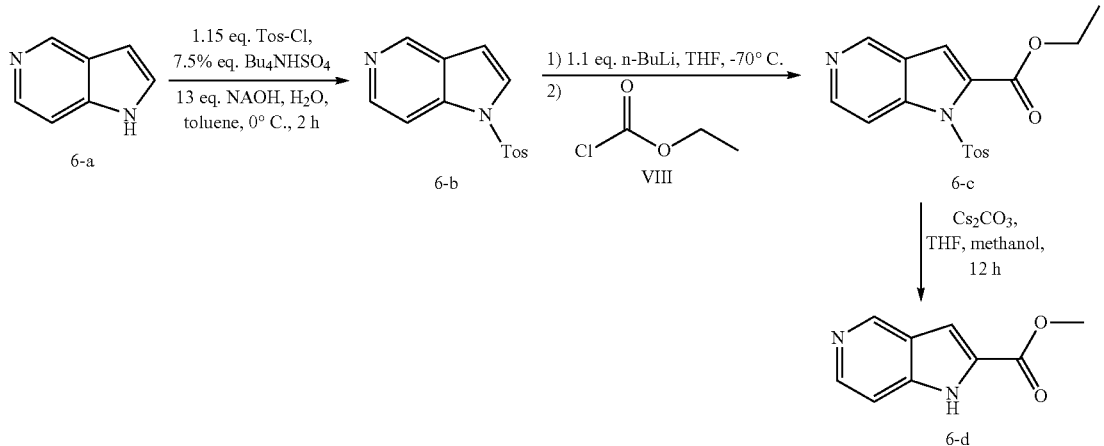

Step 1: Synthesis of 1-tosyl-1H-pyrrolo[3,2-c]pyridine (6-b)

To a mixture of compound 6-a (CAS 271-34-1) (30 g, 253 mmol), Tos-Cl (CAS 98-59-9) (55.5 g, 291 mmol) and Bu$_4$NHSO$_4$ (CAS 2472-88-0) (0.63 g, 1.9 mmol) in toluene (690 mL), a solution of NaOH (CAS 1310-73-2) (132 g, 3300 mmol) in water (690 mL) was added at 0° C. The reaction mixture was stirred under nitrogen at 10° C. for 2 hours. Water (1000 mL) was added, then the mixture was extracted with ethyl acetate (2000 mL×2). The combined organic layer was washed with brine, dried over Na$_2$SO$_4$. The solvent was evaporated under vacuum and the residue was washed with tert-butylmethyl ether. Product 6-b was obtained as an off-white powder (64 g, 93%)

Step 2: Synthesis of ethyl 1-tosyl-1H-pyrrolo[3,2-c]pyridine-2-carboxylate (6-c)

A solution of compound 6-b (10 g, 367 mmol) in dry THF (150 mL) was cooled to −70° C. and n-BuLi (CAS 109-72-8) (2.5 M in hexane, 16.7 mL, 41.9 mmol) was added dropwise under N$_2$. The mixture was stirred at −78° C. for 1 hour and then ethyl carbonochloridate (CAS 541-41-3) (fresh redistilled, 4.2 mL, 44 mmol) was added dropwise at −70° C. The mixture was warmed to 20° C. naturally and stirred at 20° C. for 1 hour. Then water (800 mL) was added. The mixture was acidified to pH=4 to 5 with a 1N HCl aqueous solution and extracted with ethyl acetate (400 mL×2). Then the pH of the aqueous layer was adjusted to pH=8 by addition of NaHCO$_3$. The resulting mixture was extracted with ethyl acetate (200 mL). The combined organic layers were washed with brine, dried over Na$_2$SO$_4$ and evaporated. The residue was washed with tert-butylmethyl ether. The solid was dried under high vacuum. The residue was purified by flash column chromatography, eluting with petroleum ether/ethyl acetate (3:2). After evaporation of the fractions, 6-c is obtained (6 g, 47%).

Step 3: Synthesis of methyl 1H-pyrrolo[3,2-c]pyridine-2-carboxylate (6-d)

A mixture of compound 6-c (6 g, 17.4 mmol) and Cs$_2$CO$_3$ (CAS 534-17-8) (17 g, 52.2 mmol) in methanol (70 mL) and THF (140 mL) was stirred at 15° C. for 12 h. The solvent was removed under vacuum. H$_2$O (30 mL) was added and the mixture was extracted with ethyl acetate (30 mL×3). The organic layer was washed with brine and dried over Na$_2$SO$_4$. The solvent was evaporated under vacuum to yield product 6-d as a white powder (1.39 g, 46%).

Scheme 7: Synthesis of tert-butyl(4-chlorobutoxy)dimethylsilane (7-c)

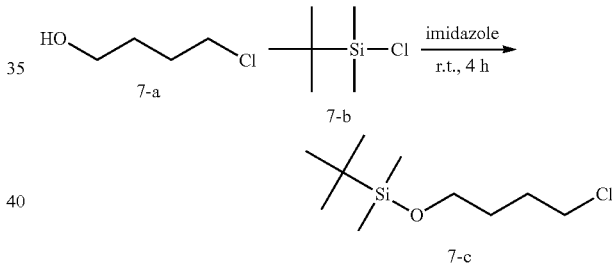

Step 1: Synthesis of tert-butyl(4-chlorobutoxy)dimethylsilane (7-c)

Compound 7-a, 4-chloro-1-butanol, (CAS 928-51-8) (100 g, 920 mmol) was dissolved in CH$_2$Cl$_2$ (1000 mL) at room temperature. Imidazole (CAS 288-32-4) (81.5, 1200 mmol) and TBDMS-Cl (CAS 18162-48-6) (152 g, 1010 mmol) was added at 0° C. The mixture was stirred for 4 h at rt. The mixture was filtered off. The filtrate was washed with 10% aqueous HCl-solution and brine. After evaporation of the filtrate, we get the product 7-c as a clear oil (100 g, 50%).

Scheme 8: Synthesis of (1-(4-(tert-butyldimethylsilyloxy)butyl)-1H-pyrrolo[3,2-c]pyridin-2-yl)methanol (8-b)

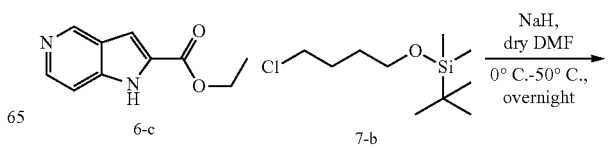

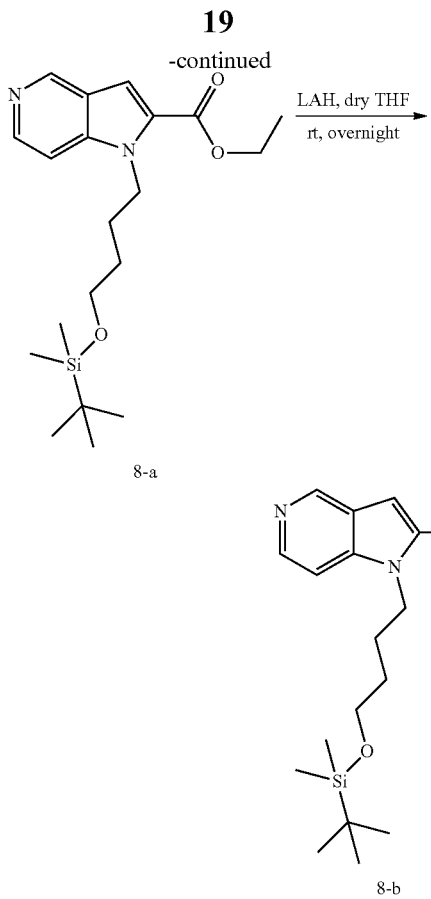

8-a

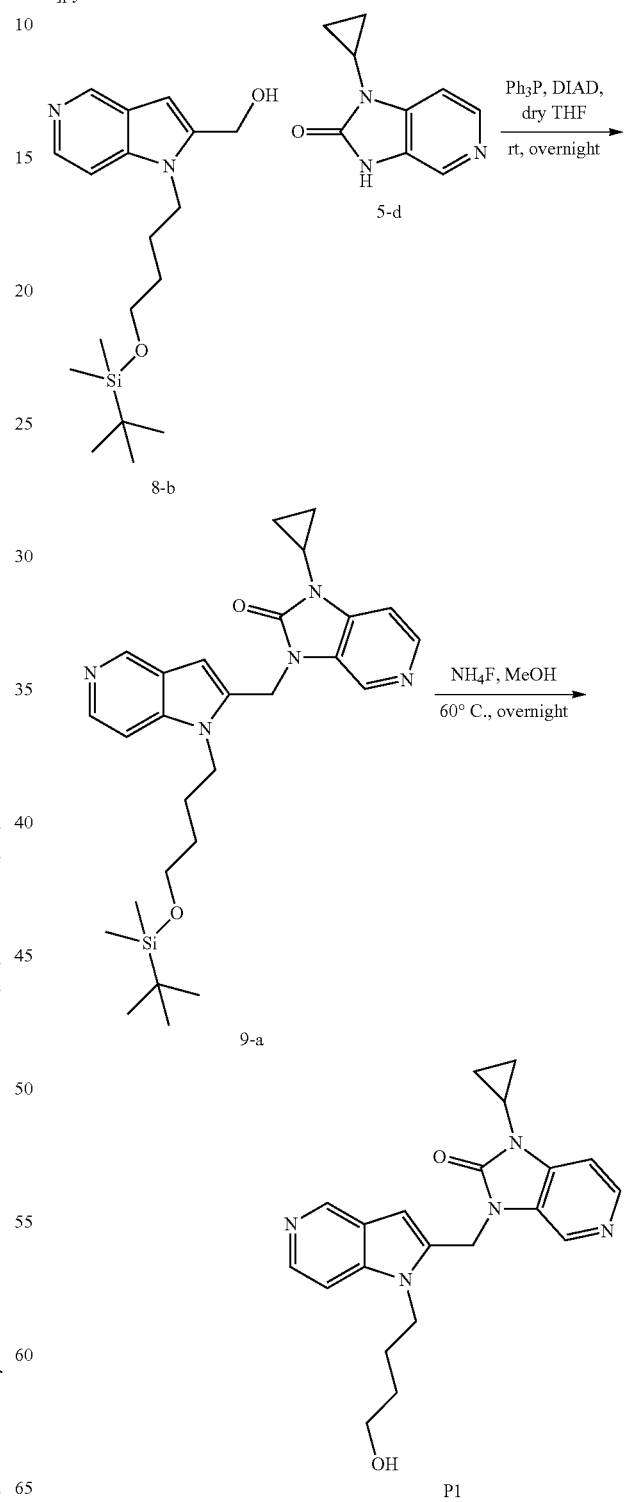

sure. The product was purified by flash column chromatography, eluting with heptane/ethyl acetate. After evaporation compound 8-b was obtained as a colorless oil (980 mg, 93%).

Scheme 9: Synthesis of 1-Cyclopropyl-3-{[1-(4-hydroxybutyl)-1H-pyrrolo[3,2-c]pyridin-2-yl]methyl}-1,3-dihydro-2H-imidazo[4,5-c]pyridin-2-one P1

Step 1: Synthesis of ethyl 1-(4-(tert-butyldimethylsilyloxy)butyl)-1H-pyrrolo-[3,2-c]pyridine-2-carboxylate (8-a)

The intermediate 6-c (1.39 g, 7.89 mmol) was dissolved in DMF (20.1 mL). The solution was cooled to 0° C., then NaH (7646-69-7) (60% suspension in mineral oil, 473.3 mg, 11.8 mmol) was added. After the mixture had stirred at 0° C. for 1 hour, 7-b (3.47 g, 15.6 mmol) was added. The resulting mixture was warmed slowly to room temperature, and then warmed at 60° C. for 12 h. The mixture was poured into an ice water solution and extracted with ethyl acetate. The organic layer was dried over MgSO$_4$, filtered and concentrated to yield a brown crude oil. The crude was purified by flash column chromatography, eluting with methanol/CH$_2$Cl$_2$ to yield compound 8-a as a solid (305 mg, 40%).

Step 2: Synthesis of (1-(4-(tert-butyldimethylsilyloxy)butyl)-1H-pyrrolo[3,2-c]-pyridin-2-yl)methanol 8-b To a solution of 8-a (1.14 g, 3.14 mmol) in dry THF (100 mL) was added drop wise LAH (CAS 16853-85-3) (a 2M solution in THF, 1.89 mL, 3.77 mmol) at room temperature. The resulting mixture was stirred at room temperature for 16 hours. The reaction mixture was quenched by addition of ethyl acetate and methanol. Then it was poured into an ice water solution. The resulting mixture was filtered on celite and the two layers were separated. The aqueous layer was extracted with ethyl acetate (2×100 mL). The combined organic extracts were washed with brine (100 mL), dried over MgSO$_4$, filtered and concentrated under reduced pres- Step 1: Synthesis of 3-((1-(4-(tert-butyldimethylsilyloxy)butyl)-1H-pyrrolo[3,2-c]-pyridin-2-yl)methyl)-1-cyclopropyl-1H-imidazo[4,5-c]pyridin-2(3H)-one 9-a To a solution of intermediate 8-b (980 mg, 2.6 mmol) and intermediate 5-d (693 mg, 3.96 mmol) in dry THF (215 mL) was added Ph₃P (CAS 603-35-0) (760 mg, 2.9 mmol) followed by DIAD (CAS 2446-83-5) (0.215 mL, 2.64 mmol) at room temperature in an inert atmosphere. The reaction mixture was stirred at room temperature overnight. The solvent was removed and the residue was purified by flash column chromatography eluting with methanol/$CH_2Cl_2$. After evaporation we get compound 9-a (950 mg, 73%).

Step 2: Synthesis of 1-Cyclopropyl-3-{[1-(4-hydroxybutyl)-1H-pyrrolo[3,2-c]-pyridin-2-yl]methyl}-1,3-dihydro-2H-imidazo[4,5-c]pyridin-2-one P1

To a solution of 9-a (950 mg, 1.21 mmol, 63% purity) in methanol (74 mL) was added $NH_4F$ (CAS 12125-01-8) (224.8 mg, 6.0 mmol). The mixture was stirred at 60° C. for 40 h. The reaction mixture was allowed to cool down to room temperature and it was then concentrated. The residue was purified by preparative column chromatography (Prep SFC on (Chiralpak Diacel OJ 20×250 mm), mobile phase ($CO_2$, methanol with 0.2% $iPrNH_2$)). The desired fractions were evaporated, the residue was redissolved in methanol and evaporated again, to yield compound P1 as a white solid (147 mg, 31%).

Example 1a

Scheme 10: synthesis of (5-chloro-1-(4-fluorobutyl)-1H-pyrrolo[2,3-c]pyridin-2-yl)methanol 10

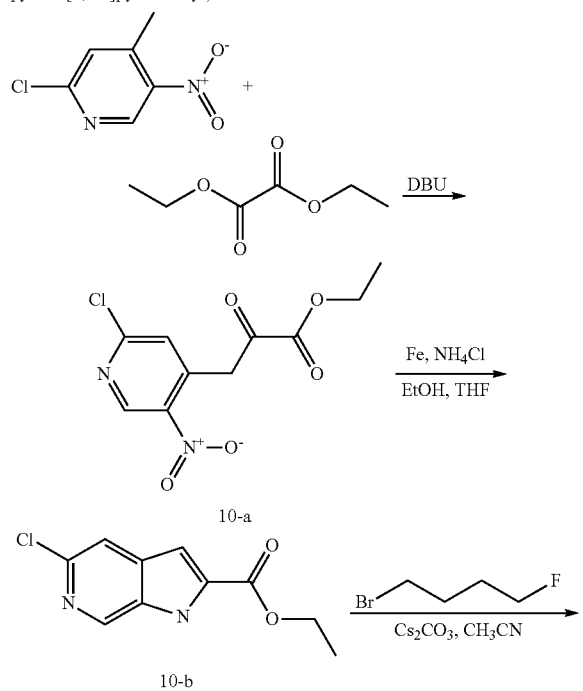

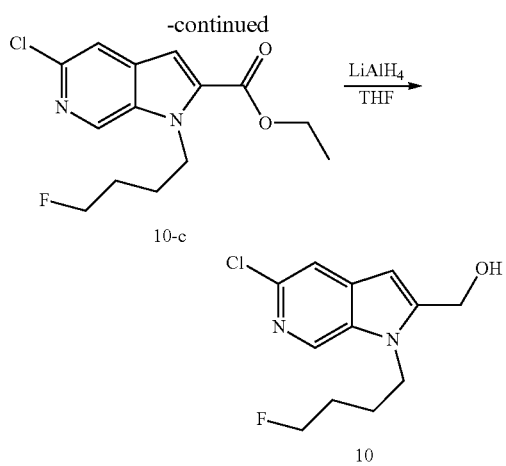

Step 1: synthesis of ethyl 3-(2-chloro-5-nitropyridin-4-yl)-2-oxopropanoate 10-a To a solution of 2-Chloro-4-methyl-5-nitropyridine (20 g, 115 mmoles) in diethyl oxalate (150 mL) under a nitrogen atmosphere was added DBU (20 mL, 1.15 eq) dropwise and stirring at room temperature was continued overnight. The reaction mixture was then poured into 200 mL ice water and this mixture was acidified with 140 mL 1N HCl solution. The semi solids were allowed to fall out and the solvent on top of it was decanted off. The residue was then stirred in ice cold ethanol. The precipitate was filtered off and dried in vacuo to give 29.04 g (92% yield) of the targeted compound 10-a. m/z=273 (M+H)+; ¹H NMR (400 MHz, DMSO-d₆)™ ppm 1.30 (t, J=7.0 Hz, 3H), 4.32 (q, J=7.1 Hz, 2H), 4.68 (s, 2H), 6.68 (s, 1H), 7.80 (s, 1H), 8.25 (s, 1H), 9.00 (s, 1H), 9.14 (s, 1H).

Step 2: synthesis of ethyl 5-chloro-1H-pyrrolo[2,3-c]pyridine-2-carboxylate 10-b To a solution of ethyl 3-(2-chloro-5-nitropyridin-4-yl)-2-oxopropanoate 10-a (2.726 g, mmoles) in THF (80 mL) and EtOH (30 mL) was added a saturated solution of ammonium chloride (50 mL). Then, iron (2.747 g, 4.9 eq) was added portionwise under vigorous stirring to the mixture at room temperature, which was subsequently heated at reflux for 2 h. The mixture was cooled down to RT, filtered over dicalite and washed with warm THF/ethanol 1/1. The filtrate was evaporated and the residue was stirred and refluxed in 100 mL water. The resulting precipitate was filtered off hot, washed twice with warm water and then dried in vacuo to provide 1.9 g (84% yield) of the targeted compound 10-b. m/z=225 (M+H)+; ¹H NMR (400 MHz, DMSO-d₆)™ ppm 1.36 (t, J=6.8 Hz, 3H), 4.39 (q, J=6.7 Hz, 2H), 7.15 (s, 1H), 7.76 (s, 1H), 8.64 (s, 1H), 12.59 (br s, 1H).

Step 3: synthesis of ethyl 5-chloro-1-(4-fluorobutyl)-1H-pyrrolo[2,3-c]pyridine-2-carboxylate 10-c To a solution of ethyl 5-chloro-1H-pyrrolo[2,3-c]pyridine-2-carboxylate 10-b (1.9 g, 8.458 mmoles) in acetonitrile (85 mL) was added cesium carbonate (3.306 g, 1.2 eq). This mixture was stirred at room temperature for one hour and then 1-bromo-4-fluorobutane (1.089 g, 1.2 eq) was added and stirring at 60° C. continued overnight. The reaction mixture was filtered over a glass filter and the filtrate was evaporated to dryness. The residue was taken up in dichloromethane and washed with water twice. The organic layer was dried over MgSO₄, filtered and evaporated. The residue was recrystallised from diisopropylether. The crystals were collected by filtration and dried in vacuo to give 2.19 g (87% yield) of the targeted compound 10-c. m/z=299 (M+H)+.

Step 4: synthesis of (5-chloro-1-(4-fluorobutyl)-1H-pyrrolo[2,3-c]pyridin-2-yl)methanol 10

To a solution of ethyl 5-chloro-1-(4-fluorobutyl)-1H-pyrrolo[2,3-c]pyridine-2-carboxylate 10-c (2.19 g, 7.3 mmoles) in THF (150 mL) was added lithium aluminium hydride (8.064 mL, 1.1 eq, 1M in THF) at −75° C. under a nitrogen atmosphere. The reaction was allowed to stir on the cooling bath for two hours while it was slowly warming up until 0° C. Then the mixture was cooled on an ice ethanol bath and carefully decomposed by adding 150 mL ethylacetate followed by 10 g of Na₂SO₄.10H₂O. The mixture was stirred for one hour and then dried over MgSO₄, filtered off and the filtrate was evaporated. The residue was purified over silica with dichloromethane/methanol 95/5 as eluent to give 550 mg (30% yield) of the targeted compound 10. m/z=257 (M+H)+.

Example 1b

Scheme 11: synthesis of (5-chloro-1-(4-fluorobutyl)-1H-pyrrolo[3,2-b]pyridin-2-yl)methanol 11

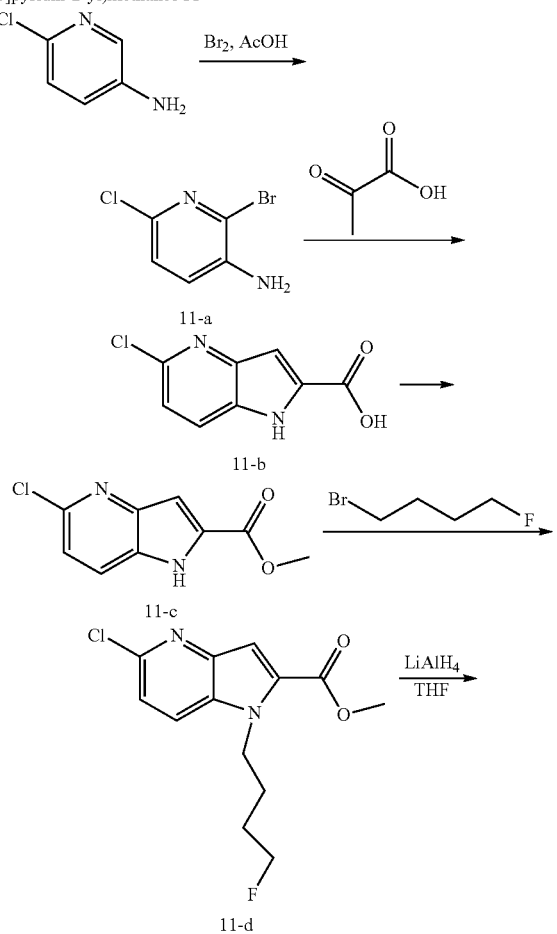

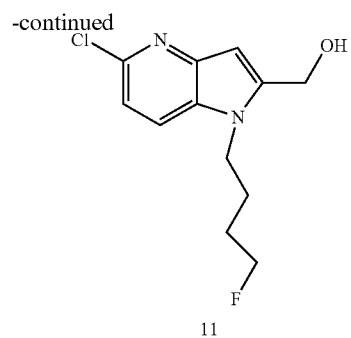

Step 1: synthesis of 2-bromo-6-chloropyridin-3-amine 11-a

Bromine (24.86 g, 155.57 mmol) was added to a solution of 6-chloropyridin-3-amine (20.00 g, 155.57 mmol) and sodium acetate (25.52 g, 311.14 mmol) in acetic acid (383 ml). The reaction mixture was stirred at room temperature for 1 hour. Acetic acid was then evaporated. The residue was dissolved in EtOAc, washed with saturated aqueous Na₂CO₃, water and brine. The organic layer was dried over MgSO₄, filtered and evaporated, yielding 32.20 g of the desired product 11-a (99.8%). m/z=206.96 (M+H)⁺, Cl+Br pattern.

Step 2: synthesis of 5-chloro-1H-pyrrolo[3,2-b]pyridine-2-carboxylic acid 11-b 2-oxopropanoic acid (36.22 g, 411.31 mmol), palladium (II)acetate (7.74 g, 34.15 mmol) and Et₃N (69.11 g, 682.94 mmol) were added to a solution of 2-bromo-6-chloropyridin-3-amine 11-a (32.20 g, 155.21 mmol) and TPP (35.83 g, 136.59 mmol) in dry DMF (300 ml). The reaction mixture was stirred at 100° C. overnight. The solvent was then evaporated, water was added and the water layer was washed with EtOAc. The water layer was acidified with conc. HCl. The precipitate was filtered off and dried, yielding 25.21 g of the wanted product 11-b (82.6%). m/z=197.1 (M+H)⁺, Cl pattern.

Step 3: synthesis of methyl 5-chloro-1H-pyrrolo[3,2-b]pyridine-2-carboxylate 11-c 5-chloro-1H-pyrrolo[3,2-b]pyridine-2-carboxylic acid 11-b (25.20 g, 128.18 mmol) was added to a refluxing mixture of sulfuric acid (20 ml) and methanol (400 ml). The mixture was refluxed overnight. The mixture was then evaporated and a cold NaHCO₃ solution was added until basic pH. The precipitate was filtered off and dried, yielding 16.15 g of the desired product (59.8%). m/z=211.17 (M+H)⁺, Cl pattern.

Step 4: synthesis of methyl 5-chloro-1-(4-fluorobutyl)-1H-pyrrolo[3,2-b]pyridine-2-carboxylate 11-d To a solution of methyl 5-chloro-1H-pyrrolo[3,2-b]pyridine-2-carboxylate 11-c (2.9 g, 12.2 mmol) in DMF (50 mL) were added successively cesium carbonate (4 g, 12.2 mmol) and 1-bromo-4-fluorobutane (1.3 mL, 12.2 mmol). The resulting mixture was heated at 60° C. overnight. The reaction mixture was allowed to cool down to room temperature then poured into iced water and the product was extracted 3 times with DCM. The combined organic layers were dried over $Na_2SO_4$, filtered and evaporated to give the targeted product 11-d as a yellowish solid. The product was used as such in the next step. m/z=313 $(M+H)^+$, Cl pattern.

Step 5: synthesis of (5-chloro-1-(4-fluorobutyl)-1H-pyrrolo[3,2-b]pyridin-2-yl)methanol 11

To a solution of methyl 5-chloro-1-(4-fluorobutyl)-1H-pyrrolo[3,2-b]pyridine-2-carboxylate 11-d (3.82 g, 10.8 mmol) in dry THF (100 mL) was added a 1M solution of lithium aluminumhydride (11.96 mL, 11.96 mmol) at −75° C. The cooling bath was then removed and the reaction mixture was kept at room temperature for 3 hours. EtOAc was added, followed by a saturated $NH_4Cl$ solution. The mixture was stirred for 30 min. The organic layer was dried over $Na_2SO_4$, filtered and evaporated to give a yellow oil, which was purified by column chromatography to yield the targeted product (5-chloro-1-(4-fluorobutyl)-1H-pyrrolo[3,2-b]pyridin-2-yl)methanol 11 (2.8 g, 98%). m/z=257 $(M+H)^+$, Cl pattern.

mixture was filtered through a celite pad. The filtrate was purified by flash column (Eluent: petroleum ether:ethyl acetate=3:1 and then ethyl acetate:methanol=10:1) to yield the intermediate 12-a (75 g, 29%).

Step 2: Synthesis of 1-bromo-3-(methylsulfonyl)propane 12-b

The intermediate 12-a (75 g, 543 mmol) was dissolved in $CH_2Cl_2$ (750 mL). The mixture was cooled to 0° C. Then phosphorus tribromide (53.6 mL, 570 mmol) was added dropwise keeping the temperature between 0 and 5° C. After addition, the mixture was allowed to warm to 25° C. and stirred for 15 h. The mixture was poured into ice-water. The separated organic layer was washed with brine (2×500 mL), dried over $Na_2SO_4$, filtered and evaporated under vacuum to yield the title compound 12-b (77 g, 71%). $^1$H NMR (400 MHz, CHLOROFORM-d) δ ppm 2.25-2.40 (m, 2H) 2.91 (s, 3H) 3.1-3.2 (m, 2H) 3.5-3.6 (m, 2H).

Scheme 12: synthesis of (3-bromo-1-(3-methylsulfonyl)propyl)-1H-pyrrolo[3,2-c]pyridin-2-yl)methanol 12

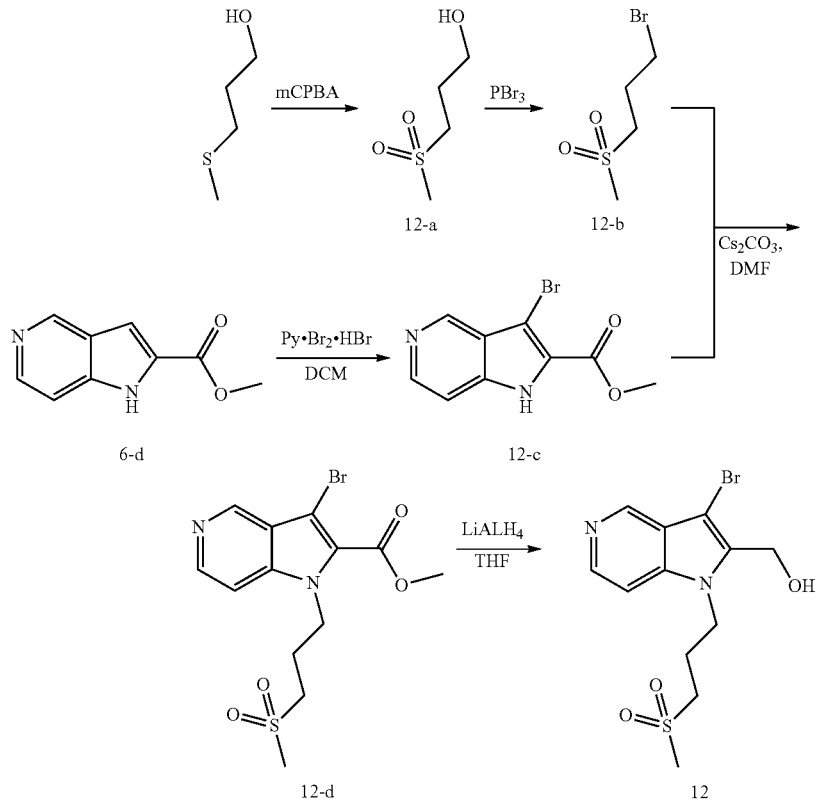

Step 1: Synthesis of 3-(methylsulfonyl)propan-1-ol 12-a 3-(methylthio)propan-1-ol (200 g, 1900 mmol, CAS 505-10-2) was dissolved in $CH_2Cl_2$ (2000 mL). The mixture was cooled to 0° C. Then m-CPBA 85% in water (970 g, 5700 mmol, CAS 937-14-4) was added portion wise keeping the temperature between 0 and 5° C. After addition, the mixture was allowed to warm to 25° C. and stirred for 15 h. The

Step 3: synthesis of methyl 3-bromo-1H-pyrrolo[3,2-c]pyridine-2-carboxylate 12-c To a mixture of methyl 1H-pyrrolo[3,2-c]pyridine-2-carboxylate 6-d (30 g, 96 mmoles) in DCM (300 mL) was added pyridinium tribromide (38 g, 1 eq) at 0° C. The mixture was warmed to room temperature and stirred for 12 h. The solid was filtrated and washed with DCM (200 ml).

The filtrate was evaporated under vacuum and the resulting residue was purified by high-performance liquid chromatography (C18, eluent: $CH_3OH/H_2O$ from 15/85 to 45/55 with 0.1% TFA as buffer). The pure fractions were collected and the volatiles were removed under vacuum and the aqueous solution was basified with $NaHCO_3$ to pH=8. The residue was extracted with DCM (100 ml*2). The organic layer was washed with brine (100 ml) and dried over $Na_2SO_4$. The solvent was removed under vacuum and the residue was washed with t-butyl methyl ether (10 ml) and ethyl acetate (10 ml). The resulting solid was dried under high vacuum to give 2.43 g (11%) of the targeted product 12-c. m/z=256 (M+H)$^+$.

Step 4: synthesis of methyl 3-bromo-1-(3-(methylsulfonyl)propyl)-1H-pyrrolo[3,2-c]pyridine-2-carboxylate 12-d A suspension of methyl 3-bromo-1H-pyrrolo[3,2-c]pyridine-2-carboxylate 12-c (1000 mg, 3.92 mmol), 1-bromo-3-(methylsulfonyl)propane 12-b (804 mg, 3.92 mmol) and cesium carbonate (1277 mg, 3.92 mmol) in dry DMF (8 ml) was heated at 60° C. for 2 hours. The reaction mixture was then cooled to room temperature and poured into iced water. The product was extracted three times with DCM. The combined organic layers were dried over $Na_2SO_4$, filtered and evaporated to dryness. The crude was purified by column chromatography using a gradient starting from 0% to 10% MeOH/DCM. After evaporation and drying in vacuo, 750 mg (2.0 mmol, 51.0%) of the target product 12-d was obtained as a white solid. $^1$H NMR (400 MHz, DMSO-$d_6$) δ ppm 2.10-2.23 (m, 2H) 2.97 (s, 3H) 3.13-3.22 (m, 2H) 3.95 (s, 3H) 4.65 (t, J=7.28 Hz, 2H) 7.75 (dd, J=6.02, 1.00 Hz, 1H) 8.47 (d, J=6.02 Hz, 1H) 8.88 (d, J=1.00 Hz, 1H); m/z=375 (M+H)$^+$, Br pattern.

Step 5: synthesis of (3-bromo-1-(3-(methylsulfonyl)propyl)-1H-pyrrolo[3,2-c]pyridin-2-yl)methanol 12

Methyl 3-bromo-1-(3-(methylsulfonyl)propyl)-1H-pyrrolo[3,2-c]pyridine-2-carboxylate 12-d (750 mg, 1.554 mmol) was dissolved in dry THF (16 ml), the solution was placed under $N_2$ atmosphere and cooled to −78° C. Then a 1 M solution of lithium aluminum hydride (1.865 ml, 1.865 mmol) in THF was added dropwise at −78° C. Then the cooling bath was removed and the reaction mixture was slowly warmed to room temperature. The mixture was stirred at room temperature for 1 hour. Then EtOAc was added carefully followed by an aqueous solution of saturated ammonium chloride. The mixture was stirred for 30 minutes, then the product was extracted with ethyl acetate. The combined organic layers were dried over $Na_2SO_4$ and concentrated to get 200 mg (0.576 mmol, 37.1%) of the product as a white solid. The water layer was evaporated and the residue was stirred in MeOH. The suspension was filtered and the filtrate was evaporated to dry on silica. This crude was purified by column chromatography using a gradient starting from 0% to 10% MeOH/DCM. After evaporation and drying in vacuo, 140 mg (0.403 mmol, 25.9%) of the target product 12 was obtained as a white solid. m/z=347 (M+H)$^+$, Br pattern.

Example 1d

Synthesis of 3-((3-bromo-1-(3-(methylsulfonyl)propyl)-1H-pyrrolo[3,2-c]pyridin-2-yl)methyl)-1-cyclopropyl-1H-imidazo[4,5-c]pyridin-2(3H)-one P17

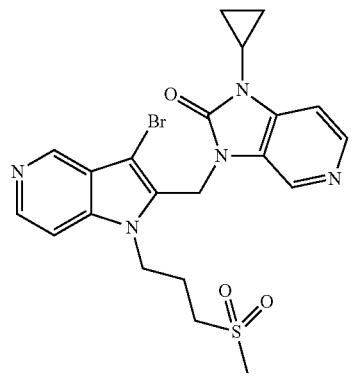

P17

A solution of (3-bromo-1-(3-(methylsulfonyl)propyl)-1H-pyrrolo[3,2-c]pyridin-2-yl)methanol 12 (200 mg, 0.576 mmol), 1-cyclopropyl-1H-imidazo[4,5-c]pyridin-2(3H)-one (101 mg, 0.576 mmol) and triphenylphosphine (151 mg, 0.576 mmol) in dry THF (4 ml) was placed under $N_2$ atmosphere. Then diisopropylazodicarboxylate (DIAD) (113 μl, 0.576 mmol) was added at room temperature. The reaction mixture was stirred at room temperature overnight. The formed solid was filtered off and washed with diethyl ether to give 83 mg of the desired product P17 as a white powder (0.165 mmol, 27.0%). $^1$H NMR (400 MHz, DMSO-$d_6$) δ ppm 0.89-0.98 (m, 2H) 1.03-1.12 (m, 2H) 1.74-1.88 (m, 2H) 2.92 (s, 3H) 3.00 (tt, J=6.84, 3.45 Hz, 1H) 3.07 (t, J=7.30 Hz, 2H) 4.39 (t, J=7.65 Hz, 2H) 5.35 (s, 2H) 7.28 (d, J=5.27 Hz, 1H) 7.62 (d, J=5.77 Hz, 1H) 8.23 (s, 1H) 8.24 (d, J=5.27 Hz, 1H) 8.36 (d, J=6.02 Hz, 1H) 8.75 (s, 1H); m/z=504 (M+H)$^+$, Br pattern.

Example 1e

Synthesis of 3-((5-chloro-1-(4-fluorobutyl)-1H-pyrrolo[3,2-b]pyridin-2-yl)methyl)-1-cyclopropyl-1H-imidazo[4,5-c]pyridin-2(3H)-one P42

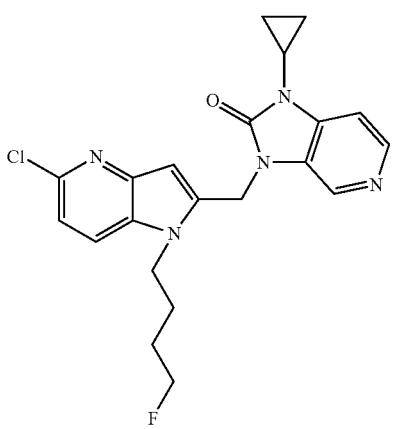

P42

3-((5-chloro-1-(4-fluorobutyl)-1H-pyrrolo[3,2-b]pyridin-2-yl)methyl)-1-cyclopropyl-1H-imidazo[4,5-c]pyridin-2(3H)-one P42 was synthetized following the procedure reported for the synthesis of 3-((3-bromo-1-(3-(methylsulfonyl)propyl)-1H-pyrrolo[3,2-c]pyridin-2-yl)methyl)-1-cyclopropyl-1H-imidazo[4,5-c]pyridin-2(3H)-one P17, using (5-chloro-1-(4-fluorobutyl)-1H-pyrrolo[3,2-b]pyridin-2-yl)methanol 11 instead of (3-bromo-1-(3-(methylsulfonyl)propyl)-1H-pyrrolo[3,2-c]pyridin-2-yl)methanol 12. $^1$H NMR (400 MHz, DMSO-$d_6$) δ ppm 0.88-0.96 (m, 2H) 1.03-1.12 (m, 2H) 1.47-1.72 (m, 4H) 2.98 (tt, J=6.93, 3.61 Hz, 1H) 4.18-4.53 (m, 4H) 5.34 (s, 2H) 6.69 (s, 1H) 7.18 (d, J=8.53 Hz, 1H) 7.28 (d, J=5.02 Hz, 1H) 8.01 (d, J=8.53 Hz, 1H) 8.25 (d, J=5.27 Hz, 1H) 8.39 (s, 1H).

Example 1f

Synthesis of 3-((5-chloro-1-(4-fluorobutyl)-1H-pyrrolo[2,3-c]pyridin-2-yl)methyl)-1-cyclopropyl-1H-imidazo[4,5-c]pyridin-2(3H)-one P11

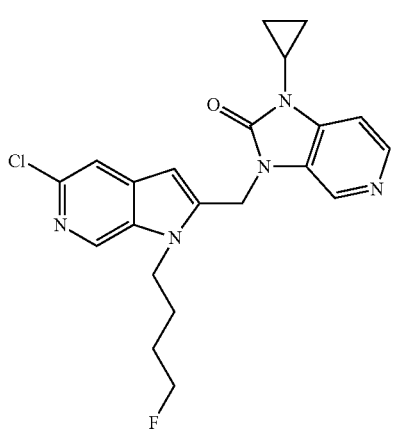

P11

3-((5-chloro-1-(4-fluorobutyl)-1H-pyrrolo[2,3-c]pyridin-2-yl)methyl)-1-cyclopropyl-1H-imidazo[4,5-c]pyridin-2(3H)-one P11 was synthetized following the procedure reported for the synthesis of 3-((3-bromo-1-(3-(methylsulfonyl)propyl)-1H-pyrrolo[3,2-c]pyridin-2-yl)methyl)-1-cyclopropyl-1H-imidazo[4,5-c]pyridin-2(3H)-one P17, using (5-chloro-1-(4-fluorobutyl)-1H-pyrrolo[2,3-c]pyridin-2-yl)methanol 10 instead of (3-bromo-1-(3-(methylsulfonyl)propyl)-1H-pyrrolo[3,2-c]pyridin-2-yl)methanol 12. $^1$H NMR (360 MHz, DMSO-$d_6$) δ ppm 0.87-0.97 (m, 2H), 1.02-1.13 (m, 2H), 1.57-1.78 (m, 4H), 2.99 (tt, J=6.9, 3.6 Hz, 1H), 4.30-4.43 (m, 3H), 4.49 (m, J=5.7, 5.7 Hz, 1H), 5.35 (s, 2H), 6.53 (s, 1H), 7.29 (d, J=5.5 Hz, 1H), 7.56 (s, 1H), 8.26 (d, J=5.1 Hz, 1H), 8.37 (s, 1H), 8.70 (s, 1H); m/z=414 (M+H)$^+$.

Example 2

Characterization of Compounds, and Test for RSV Inhibitory Activity

General Experimental Details

HPLC-MS analysis was done using either one of the following methods:

Method 1:

The HPLC measurement was performed using an Agilent 1100 module comprising a pump, a diode-array detector (DAD) (wavelength used 220 nm), a column heater and a column as specified below. Flow from the column was split to an Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 mL were used. Oven temperature was 50° C. (MS polarity: positive)

Method 2:

The HPLC measurement was performed using an Agilent 1100 module comprising a pump, a diode-array detector (DAD) (wavelength used 220 nm), a column heater and a column as specified below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 mL were used. Oven temperature was 50° C. (MS polarity: positive)

Method 3:

Column: XTerra MS C18 2.5µ, 4.6×50 mm, mobile phase A: 10 mM NH$_4$OOCH+0.1% HCOOH in water, mobile phase B: methanol operating at a column temperature of 50° C. using a flow rate of 1.5 mL/min. Gradient conditions: t=0 min: 65% A, 35% B; t=3.5 min, 5% A, 95% B; t=5.5 min, 5% A, 95% B; t=5.6 min: 65% A, 35% B; t=7 min, 65% A, 35% B.

Method 4:

Column: SunFire C18 3.5µ 4.6×100 mm, mobile phase A: 10 mM NH$_4$OOCH+0.1% HCOOH in water, mobile phase B: methanol operating at a column temperature of 50° C. using a flow rate of 1.5 mL/min. Gradient conditions: t=0 min: 65% A, 35% B; t=7 min, 5% A, 95% B; t=9.6 min, 5% A, 95% B; t=9.8 min: 65% A, 35% B; t=12 min, 65% A, 35% B.

NMR spectra were recorded on a Bruker Avance 400 spectrometer, operating at 400 MHz for $^1$H. Chemical shifts are given in ppm and a J value in Hz. Multiplicity is indicated using the following abbreviations: d for doublet, t for a triplet, m for a multiplet, etc. Thin-layer chromatography (TLC) was performed on 5×10 cm aluminium sheets coated with Silicagel 60 F$_{254}$ (Merck KGaA).

Antiviral Activity

Black 96-well clear-bottom microtiter plates (Corning, Amsterdam, The Netherlands) were filled in duplicate using a customized robot system with serial 4-fold dilutions of compound in a final volume of 50 µl culture medium [RPMI medium without phenol red, 10% FBS, 0.04% gentamycin (50 mg/mL) and 0.5% DMSO]. Then, 100 μl of a HeLa cell suspension (5×10$^4$ cells/mL) in culture medium was added to each well followed by the addition of 50 μl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% $CO_2$ atmosphere. Three days post-virus exposure, viral replication was quantified by measuring GFP expression in the cells by a MSM laser microscope (Tibotec, Beerse, Belgium). The $EC_{50}$ was defined as the 50% inhibitory concentration for GFP expression. In parallel, compounds were incubated for three days in a set of white 96-well microtiter plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity.

REFERENCES

Hallak L K, Spillmann D, Collins P L, Peeples M E. Glycosaminoglycan sulfation requirements for respiratory syncytial virus infection. J. Virol. 740, 10508-10513 (2000).

Example 3

Derivatives P2 to P10, P11-P26, P29-P30, P32-44 were prepared according to the methods described above. Compounds were tested for RSV inhibitory activity. The results are depicted in the tables 1 to 3 below, with reference to formula Ia with ring atoms numbered as follows:

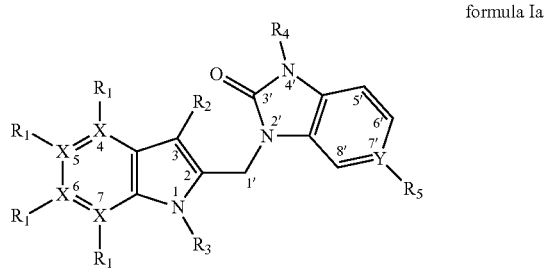

formula Ia

TABLE 1

| | Compound name | $X_4$—$R_1$ | $X_5$—$R_1$ | $X_6$—$R_1$ | $X_7$—$R_1$ | $R_2$ | $R_3$ |
|---|---|---|---|---|---|---|---|
| P1 | 1-Cyclopropyl-3-{[1-(4-hydroxybutyl)-1H-pyrrolo[3,2-c]pyridin-2-yl]methyl}-1,3-dihydro-2H-imidazo[4,5-c]pyridin-2-one | C—H | N | C—H | C—H | H | ~~~~\_/\_/\_OH |
| P2 | 3-{[5-Chloro-1-(4-hydroxybutyl)-1H-pyrrolo[3,2-b]pyridin-2-yl]methyl}-1-cyclopropyl-1,3-dihydro-2H-imidazo[4,5-c]pyridin-2-one | N | C—Cl | C—H | C—H | H | ~~~~\_/\_/\_OH |
| P3 | 1-Cyclopropyl-3-{[1-(3-methylbutyl)-1H-pyrrolo[3,2-b]pyridin-2-yl]methyl}-1,3-dihydro-2H-imidazo[4,5-c]pyridin-2-one | N | C—H | C—H | C—H | H | ~~~~\_/\_/\ |
| P4 | 1-Cyclopropyl-3-{[1-(4-hydroxybutyl)-1H-pyrrolo[2,3-c]pyridin-2-yl]methyl}-1,3-dihydro-2H-imidazo[4,5-c]pyridin-2-one | C—H | C—H | N | C—H | H | ~~~~\_/\_/\_OH |

TABLE 1-continued

| | | | | | | | |
|---|---|---|---|---|---|---|---|
| P5 | 1-Cyclopropyl-3-{[1-(4-hydroxybutyl)-1H-pyrrolo[3,2-b]pyridin-2-yl]methyl}-1,3-dihydro-2H-imidazo[4,5-c]pyridin-2-one | N | C—H | C—H | C—H | H | 4-hydroxybutyl chain |
| P6 | 1-Cyclopropyl-3-{[1-(4-hydroxybutyl)-5-methoxy-1H-pyrrolo[3,2-b]pyridin-2-yl]methyl}-1,3-dihydro-2H-imidazo[4,5-c]pyridin-2-one | N | C—OMe | C—H | C—H | H | 4-hydroxybutyl chain |
| P8 | 1-Cyclopropyl-3-{[5-hydroxy-1-(4-hydroxybutyl)-1H-pyrrolo[3,2-b]pyridin-2-yl]methyl}-1,3-dihydro-2H-imidazo[4,5-c]pyridin-2-one | N | C—OH | C—H | C—H | H | 4-hydroxybutyl chain |
| P9 | 4-{2-[(1-Cyclopropyl-2-oxo-1,2-dihydro-3H-imidazo[4,5-c]pyridin-3-yl)methyl]-5-hydroxy-1H-pyrrolo[3,2-b]pyridin-1-yl}butyl 2,2-dimethylpropanoate | N | C—OH | C—H | C—H | H | butyl pivalate ester |
| P10 | 1-Cyclopropyl-3-{[1-(3-methylbutyl)-1H-pyrrolo[2,3-b]pyridin-2-yl]methyl}-1,3-dihydro-2H-imidazo[4,5-c]pyridin-2-one | C—H | C—H | C—H | N | H | 3-methylbutyl chain |

| | R₄ | Y₇—R₅ | ¹H NMR | LC-MS | WT activity EC$_{50}$ (nM) | Toxicity CC$_{50}$ (nM) |
|---|---|---|---|---|---|---|
| P1 | cyclopropyl | N | ¹H NMR (400 MHz, CHLOROFORM-d) δ ppm 0.98-1.07 (m, 2 H) 1.13-1.21 (m, 2 H) 1.52-1.77 (m, 4 H) 1.98-2.73 (m, 1 H) 2.87-3.02 (m, 1 H) 3.64 (t, J = 5.90 Hz, 2 H) 4.19-4.31 (m, 2 H) 5.26 (s, 2 H) 6.71 (s, 1 H) 7.16 (m, J = 4.64, 4.64 Hz, 1 H) 8.18-8.32 (m, 2 H) 8.36 (s, 1 H) 8.81 (s, 1 H) | 378 (MH⁺) | 1.05 | >98360.3 |
| P2 | cyclopropyl | N | ¹H NMR (400 MHz, DMSO-d₆) δ ppm 0.86-0.98 (m, 2 H) 0.99-1.12 (m, 2 H) 1.28-1.40 (m, 2 H) 1.40-1.59 (m, 2 H) 2.92-3.04 (m, 1 H) 3.43-3.60 (m, 2 H) 4.27 (t, J = 7.40 Hz, 2 H) 4.42 (br. s., 1 H) 5.33 (s, 2 H) 6.67 (s, 1 H) 7.16 (d, J = 8.53 Hz, 1 H) | 412 (MH⁺) | 15.6 | >9836.0 |

TABLE 1-continued

| | | | | | | |
|---|---|---|---|---|---|---|
| | | | 7.27-7.47 (m, 1 H) 7.97 (d, J = 8.53 Hz, 1 H) 8.27 (d, J = 4.52 Hz, 1 H) 8.41 (s, 1 H) | | | |
| P3 | 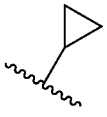 [SMILES: *C1CC1] | N | ¹H NMR (400 MHz, CHLOROFORM-d) δ ppm 0.94 (d, J = 6.63 Hz, 6 H) 1.01-1.07 (m, 2 H) 1.12-1.22 (m, 2 H) 1.34-1.43 (m, 2 H) 1.59-1.72 (m, 1 H) 2.88-2.97 (m, 1 H) 4.17-4.26 (m, 2 H) 5.28 (s, 2 H) 6.80 (s, 1 H) 7.10 (dd, J = 8.29, 4.59 Hz, 1H) 7.15 (d, J = 5.27 Hz, 1 H) 7.55 (d, J = 8.20 Hz, 1 H) 8.31 (d, J = 5.27 Hz, 1 H) 8.33-8.37 (m, 1 H) 8.44 (dd, J = 4.59, 1.27 Hz, 1 H) | 376 (MH⁺) | 62.9 | 67978.2 |
| P4 | 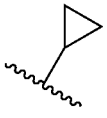 [SMILES: *C1CC1] | N | ¹H NMR (400 MHz, CHLOROFORM-d) δ ppm 1.00-1.07 (m, 2 H) 1.14-1.22 (m, 2 H) 1.52-1.90 (m, 4 H) 2.89-3.01 (m, 1 H) 4.29-4.42 (m, 2 H) 5.28 (s, 2 H) 6.63 (s, 1 H) 7.16 (d, J = 5.27 Hz, 1 H) 7.46 (d, J = 5.27 Hz, 1 H) 8.23 (d, J = 5.52 Hz, 1 H) 8.32 (d, J = 5.27 Hz, 1 H) 8.37 (s, 1 H) 8.74 (s, 1 H) | 378 (MH⁺) | 129.4 | >9836.0 |
| P5 | 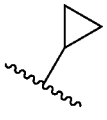 | N | ¹H NMR (400 MHz, DMSO-d₆) δ ppm 0.91-0.98 (m, 2 H) 1.04-1.13 (m, 2 H) 1.33-1.61 (m, 4 H) 2.94-3.05 (m, 1 H) 3.29-3.37 (m, 3 H) 4.27 (t, J = 7.41 Hz, 2 H) 5.34 (s, 2 H) 6.68 (s, 0 H) 7.12 (dd, J = 8.29, 4.59 Hz, 0 H) 7.28 (dd, J = 5.27, 0.59 Hz, 0 H) 7.87 (d, J = 8.20 Hz, 0 H) 8.24 (d, J = 5.27 Hz, 0 H) 8.31 (dd, J = 4.68, 1.37 Hz, 0 H) 8.39 (s, 0 H) | 378 (MH⁺) | 160.3 | >98360.3 |
| P6 | 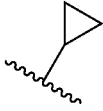 [SMILES: *C1CC1] | N | ¹H NMR (400 MHz, DMSO-d₆) δ ppm 0.88-0.98 (m, 2 H) 1.03-1.12 (m, 2 H) 1.30-1.52 (m, 4 H) 2.99 (m, J = 7.00, 3.40, 3.40 Hz, 1 H) 3.26-3.32 (m, 2 H) 3.82 (s, 3 H) 4.22 (t, J = 7.40 Hz, 2 H) 4.42 (t, J = 5.14 Hz, 1 H) 5.28 (s, 2 H) 6.49-6.63 (m, 2 H) 7.27 (dd, J = 5.14, 0.63 Hz, 1 H) 7.77-7.85 (m, 0 H) 8.24 (d, J = 5.27 Hz, 1 H) 8.38 (s, 1 H) | 408 (MH⁺) | 219.5 | >9836.0 |
| P8 | 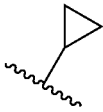 | N | ¹H NMR (400 MHz, DMSO-d₆) δ ppm 0.86-0.96 (m, 2 H) 1.02-1.11 (m, 2 H) 1.29-1.51 (m, 4 H) 2.98 (tt, J = 6.93, 3.48 Hz, 1 H) 3.33-3.40 (m, 2 H) 4.14 (t, J = 7.15 Hz, 2H) 4.42 (t, J = 5.14 Hz, 1 H) 5.18 (s, 2 H) 6.02 (d, J = 9.54 Hz, 1 H) 6.10 (s, 1 H) 7.27 (d, J = 5.27 Hz, 1 H) 7.69 (d, J = 9.54 Hz, 1 H) 8.25 (d, J = 5.27 Hz, 1 H) 8.37 (s, 1 H) 11.39 (br. s,, 1 H) | 394 (MH⁺) | 8464.9 | >9836.0 |

TABLE 1-continued

| | | | ¹H NMR | MH⁺ | | |
|---|---|---|---|---|---|---|
| P9 | (cyclopropyl) | N | ¹H NMR (400 MHz, DMSO-d₆) δ ppm 0.90-0.99 (m, 2 H) 1.01-1.19 (m, 11 H) 1.43-1.67 (m, 4 H) 3.05 (tt, J = 6.71, 3.45 Hz, 1 H) 3.75-4.05 (m, 2 H) 4.11-4.32 (m, 2 H) 5.22 (s, 2 H) 6.04 (d, J = 9.54 Hz, 1 H) 6.14 (s, 1 H) 7.53 (d, J = 5.52 Hz, 1 H) 7.74 (d, J = 9.54 Hz, 1 H) 8.42 (d, J = 5.77 Hz, 1 H) 8.55 (s, 1 H) 11.50 (br. s,, 1H) | 478 (MH⁺) | >9836.0 | >9836.0 |
| P10 | (cyclopropyl) | N | ¹H NMR (400 MHz, CHLOROFORM-d) δ ppm 0.93 (d, J = 6.44 Hz, 6 H) 1.01-1.08 (m, 2 H) 1.14-1.22 (m, 2 H) 1.43-1.52 (m, 2 H) 1.62-1.72 (m, 1 H) 2.88-2.98 (m, 1 H) 4.31-4.40 (m, 2 H) 5.27 (s, 2 H) 6.50 (s, 1 H) 7.03 (dd, J = 7.81, 4.68 Hz, 1 H) 7.15 (dd, J = 5.27, 0.59 Hz, 1 H) 7.82 (dd, J = 7.80, 1.56 Hz, 1 H) 8.27-8.38 (m, 3 H) | 376 (MH⁺) | >98360.3 | >98360.3 |

TABLE 2

| | X₄—R₁ | X₅—R₁ | X₆—R₁ | R₂ | R₃ | R₄ | Y₇—R₅ | ¹H NMR | WT activity EC₅₀ (nM) | SI CC₅₀/EC₅₀ |
|---|---|---|---|---|---|---|---|---|---|---|
| P11 | CH | C—Cl | N | H | (alkyl-F) | (cyclopropyl) | N | ¹H NMR (360 MHz, DMSO-d₆) δ ppm 0.87-0.97 (m, 2 H), 1.02-1.13 (m, 2 H), 1.57-1.78 (m, 4 H), 2.99 (tt, J = 6.9, 3.6 Hz, 1 H), 4.30-4.43 (m, 3 H), 4.49 (m, J = 5.7, 5.7 Hz, 1 H), 5.35 (s, 2 H), 6.53 (s, 1 H), 7.29 (d, J = 5.5 Hz, 1 H), 7.56 (s, 1 H), 8.26 (d, J = 5.1 Hz, 1 H), 8.37 (s, 1 H), 8.70 (s, 1 H) | 5.326 | >9387 |
| P12 | CH | C—Cl | N | H | (alkyl-CF₂F) | (cyclopropyl) | N | ¹H NMR (360 MHz, DMSO-d₆) δ ppm 0.87-0.97 (m, 2 H), 1.02-1.13 (m, 2 H), 1.73-1.87 (m, 2 H), 2.34 (m, J = 16.6, 11.2 Hz, 2 H), 2.98 (tt, J = 7.0, 3.4 Hz, 1 H), 4.44 (t, J = 7.7 Hz, 2 H), 5.36 (s, 2 H), 6.51 (s, 1 H), 7.30 (d, J = 5.1 Hz, 1 H), 7.57 (s, 1 H), 8.27 (d, J = 5.1 Hz, 1 H), 8.40 (s, 1 H), 8.75 (s, 1 H) | 2.375 | >10526 |
| P13 | CH | C—Cl | N | H | (alkyl-CF₂F) | (CF₃-CH₂) | N | ¹H NMR (360 MHz, DMSO-d₆) δ ppm 1.84 (m, J = 7.3, 7.3 Hz, 1 H), 2.25-2.41 (m, 2 H), 4.44 (t, J = 7.3 Hz, 2 H), 4.91 (q, J = 9.0 Hz, 2 H), 5.46 (s, 2 H), 6.47 (s, 1 H), 7.46 (d, J = 5.1 Hz, 1 H), 7.58 (s, 1 H), 8.33 (d, J = 5.1 Hz, 1 H), 8.49 (s, 1 H), 8.76 (s, 1 H) | 0.938 | >106591 |
| P14 | CH | C—Cl | N | H | (alkyl-CF₂F) | (CF₃-CH₂) | C—F | ¹H NMR (360 MHz, DMSO-d₆) δ ppm 1.85 (quin, J = 7.5 Hz, 2 H), 2.34 (m, J = 16.3, 11.2 Hz, 2 H), 4.45 (t, J = 7.5 Hz, 2 H), 4.87 (q, J = 9.4 Hz, 2 H), 5.40 (s, 2 H), 6.38 (s, 1 H), 6.94-7.07 (m, 1 H), 7.29 (dd, J = 9.0, 2.4 Hz, 1 H), 7.39 (m, J = 8.6, 4.6 Hz, 1 H), 7.52-7.62 (m, 1 H), 8.75 (s, 1 H) | 17.171 | >5823 |

TABLE 2-continued

| | X₄—R₁ | X₅—R₁ | X₆—R₁ | R₂ | R₃ | R₄ | Y₇— R₅ | ¹H NMR | WT activity EC₅₀ (nM) | SI CC₅₀/ EC₅₀ |
|---|---|---|---|---|---|---|---|---|---|---|
| P15 | CH | C—Cl | N | H | 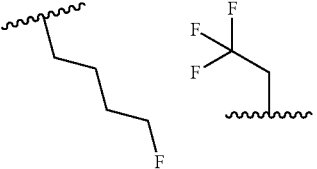 | 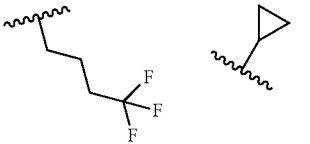 | N | ¹H NMR (360 MHz, DMSO-d₆) δ ppm 1.56-1.76 (m, 4 H), 4.31-4.45 (m, 3 H), 4.45-4.52 (m, 1 H), 4.91 (q, J = 9.1 Hz, 2 H), 5.45 (s, 2 H), 6.50 (s, 1 H), 7.46 (d, J = 5.1 Hz, 1H), 7.57 (s, 1H), 8.32 (d, J = 5.1 Hz, 1 H), 8.47 (s, 1 H), 8.71 (s, 1 H) | 1.585 | 51626 |
| P16 | CH | C—Cl | N | H | 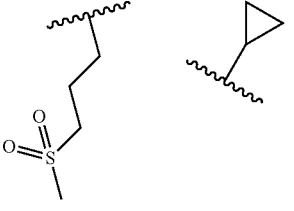 | 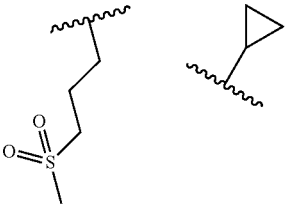 | C—F | ¹H NMR (360 MHz, DMSO-d₆) δ ppm 0.84-0.96 (m, 2 H), 0.99-1.12 (m, 2 H), 1.80 (quin, J = 8.0 Hz, 2 H), 2.25-2.43 (m, 2 H), 2.93 (tt, J = 7.0, 3.6 Hz, 1 H), 4.44 (t, J = 7.7 Hz, 2 H), 5.30 (s, 2 H), 6.42 (s, 1 H), 6.94 (ddd, J = 10.1, 8.6, 2.6 Hz, 1 H), 7.15-7.28 (m, 2 H), 7.56 (d, J = 0.7 Hz, 1H), 8.74 (s, 1 H) | 39.811 | >2730 |
| P17 | CH | N | CH | Br | 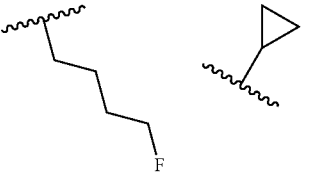 | 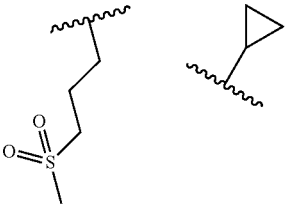 | N | ¹H NMR (400 MHz, DMSO-d₆) δ ppm 0.89-0.98 (m, 2 H) 1.03-1.12 (m, 2 H) 1.74-1.88 (m, 2 H) 2.92 (s, 3 H) 3.00 (tt, J = 6.84, 3.45 Hz, 1 H) 3.07 (t, J = 7.30 Hz, 2 H) 4.39 (t, J = 7.65 Hz, 2 H) 5.35 (s, 2 H) 7.28 (d, J = 5.27 Hz, 1 H) 7.62 (d, J = 5.77 Hz, 1 H) 8.23 (s, 1 H) 8.24 (d, J = 5.27 Hz, 1 H) 8.36 (d, J = 6.02 Hz, 1 H) 8.75 (s, 1 H) | | |
| P18 | CH | N | CH | H | 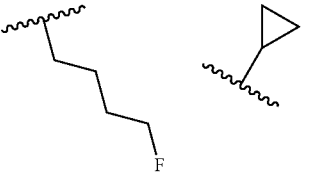 | 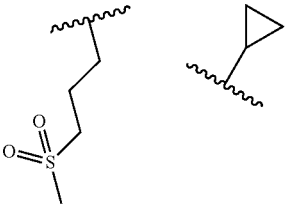 | N | ¹H NMR (400 MHz, DMSO-d₆) δ ppm 0.90-0.97 (m, 2 H) 1.03-1.11 (m, 2 H) 1.97 (m, J = 15.06, 7.78, 7.78 Hz, 2 H) 2.94-3.05 (m, 4 H) 3.16 (t, J = 8.00 Hz, 2 H) 4.43 (t, J = 7.65 Hz, 2 H) 5.36 (s, 2 H) 6.73 (s, 1 H) 7.29 (d, J = 5.27 Hz, 1 H) 7.62 (d, J = 5.52 Hz, 1 H) 8.25 (d, J = 5.27 Hz, 1 H) 8.26 (d, J = 6.02 Hz, 1 H) 8.42 (s, 1 H) 8.83 (s, 1 H) | 0.98 | >102089 |
| P19 | CH | N | CH | H | 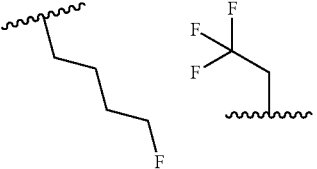 | 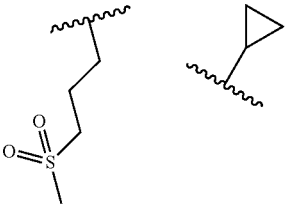 | N | 1H NMR (400 MHz, CHLOROFORM-d) δ ppm 1.00-1.07 (m, 2 H) 1.14-1.22 (m, 2 H) 1.66-1.81 (m, 4 H) 2.94 (dt, J = 6.96, 3.42 Hz, 1 H) 4.28 (t, J = 7.40 Hz, 2 H) 4.35 (s, 1 H) 4.47 (t, J = 5.40 Hz, 1 H) 5.26 (s, 2 H) 6.74 (s, 1 H) 7.15 (d, J = 5.30 Hz, 1 H) 7.18 (d, J = 6.02 Hz, 1 H) 8.31 (d, J = 6.02 Hz, 1 H) 8.32 (d, J = 5.27 Hz, 1 H) 8.36 (s, 1 H) 8.88 (d, J = 1.00 Hz, 1 H) | 0.536 | >186574 |
| P20 | CH | N | CH | H | 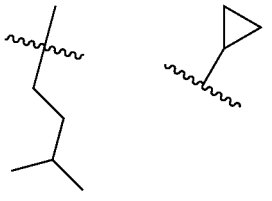 | 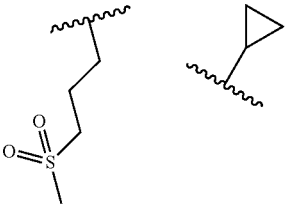 | N | ¹H NMR (360 MHz, DMSO-d₆) δ ppm 0.84-0.96 (m, 8 H), 1.03-1.14 (m, 2 H), 1.21-1.36 (m, 2 H), 1.60 (dquin, J = 13.2, 6.6, 6.6, 6.6, 6.6 Hz, 1 H), 2.98 (tt, J = 7.0, 3.5 Hz, 1 H), 4.24 (m, J = 8.1 Hz, 1 H), 5.32 (s, 2 H), 6.75 (s, 1 H), 7.29 (d, J = 5.1 Hz, 1 H), 7.41 (d, J = 5.5 Hz, 1 H), 8.19 (d, J = 5.9 Hz, 1 H), 8.24 (d, J = 5.5 Hz, 1 H), 8.38 (s, 1 H), 8.78 (s, 1 H) | 0.28 | 294002 |

TABLE 2-continued

| | X₄—R₁ | X₅—R₁ | X₆—R₁ | R₂ | R₃ | R₄ | Y₇—R₅ | ¹H NMR | WT activity EC₅₀ (nM) | SI CC₅₀/EC₅₀ |
|---|---|---|---|---|---|---|---|---|---|---|
| P21 | CH | N | CH | H | -(CH₂)₄-CF₃ | cyclopropyl | N | ¹H NMR (360 MHz, DMSO-d₆) δ ppm 0.85-0.96 (m, 2 H), 1.03-1.13 (m, 2 H), 1.70 (quin, J = 7.9 Hz, 2 H), 2.19-2.41 (m, 2 H), 2.97 (tt, J = 7.0, 3.6 Hz, 1 H), 4.35 (t, J = 7.7 Hz, 2 H), 5.34 (s, 2 H), 6.73 (s, 1 H), 7.29 (d, J = 5.1 Hz, 1 H), 7.54 (d, J = 5.5 Hz, 1 H), 8.25 (d, J = 5.1 Hz, 1 H), 8.22 (d, J = 5.9 Hz, 1 H), 8.43 (s, 1 H), 8.78 (s, 1 H) | 0.247 | >405210 |
| P22 | CH | N | CH | Cl | -(CH₂)₄-CF₃ | cyclopropyl | N | ¹H NMR (360 MHz, DMSO-d₆) δ ppm 0.85-0.94 (m, 2 H) 1.05-1.14 (m, 2 H) 1.56 (quin, J = 7.96 Hz, 2 H) 2.23 (m, J = 16.65, 11.16 Hz, 2 H) 2.95 (tt, J = 6.86, 3.57 Hz, 1 H) 4.33 (t, J = 7.68 Hz, 2 H) 5.35 (s, 2 H) 7.30 (d, J = 5.49 Hz, 1 H) 7.66 (d, J = 5.85 Hz, 1 H) 8.21-8.29 (m, 2 H) 8.35 (d, J = 5.85 Hz, 1 H) 8.84 (s, 1 H) | 4.998 | >20007 |
| P23 | CH | N | CH | F | -(CH₂)₄-CF₃ | cyclopropyl | N | ¹H NMR (360 MHz, DMSO-d₆) δ ppm 0.84-0.92 (m, 2 H) 1.03-1.12 (m, 2 H) 1.63 (quin, J = 7.87 Hz, 2 H) 2.23 (m, J = 10.98 Hz, 2 H) 2.94 (tt, J = 6.91, 3.70 Hz, 1 H) 4.32 (t, J = 7.68 Hz, 2 H) 5.35 (s, 2 H) 7.29 (d, J = 1.00 Hz, 1 H) 7.63 (dd, J = 5.85, 1.46 Hz, 1 H) 8.23-8.34 (m, 3 H) 8.91 (s, 1 H) | 29.267 | >3416 |
| P25 | CH | N | CH | Me | -(CH₂)₄-CF₃ | cyclopropyl | N | ¹H NMR (360 MHz, DMSO-d₆) δ ppm 0.88 (m, J = 5.85 Hz, 1 H) 1.08 (m, J = 6.95, 1.83 Hz, 1 H) 1.38-1.50 (m, 2 H) 2.06-2.22 (m, 2 H) 2.90-2.99 (m, 1 H) 4.21 (t, J = 7.50 Hz, 1 H) 5.30 (s, 2 H) 7.28 (d, J = 5.49 Hz, 1 H) 7.48 (d, J = 5.85 Hz, 1 H) 8.03 (s, 1 H) 8.19-8.25 (m, 2 H) 8.84 (s, 1 H) | 1.352 | >73885 |
| P26 | CH | N | CH | I | -(CH₂)₄-CF₃ | cyclopropyl | N | ¹H NMR (360 MHz, DMSO-d₆) δ ppm 0.83-0.96 (m, 2 H) 1.04-1.15 (m, 2 H) 1.51 (dt, J = 15.73, 7.87 Hz, 1 H) 2.22 (m, J = 16.65, 11.16 Hz, 1 H) 2.95 (tt, J = 6.95, 3.48 Hz, 1 H) 4.34 (t, J = 7.68 Hz, 2 H) 5.35 (s, 2 H) 7.30 (d, J = 5.12 Hz, 1 H) 7.60 (d, J = 5.49 Hz, 1 H) 8.24 (s, 1 H) 8.35 (d, J = 5.12 Hz, 1 H) 8.62 (s, 1 H) | 2.35 | 21638 |
| P29 | CH | N | CH | Br | -(CH₂)₃-S(O)(Me)- | -CH₂-CF₃ (with F) | C—F | ¹H NMR (400 MHz, DMSO-d₆) δ ppm 1.86 (m, J = 15.18, 7.72, 7.72 Hz, 2 H) 2.93 (s, 3 H) 3.03-3.16 (m, 2 H) 4.42 (t, J = 7.78 Hz, 2 H) 4.85 (q, J = 9.29 Hz, 2 H) 5.41 (s, 2 H) 6.95-7.02 (m, 1 H) 7.05 (dd, J = 9.03, 2.26 Hz, 1 H) 7.37 (dd, J = 8.53, 4.52 Hz, 1 H) 7.62 (d, J = 5.77 Hz, 1 H) 8.36 (d, J = 5.77 Hz, 1 H) 8.74 (s, 1 H) | 63.537 | 307 |
| P30 | CH | N | CH | H | -(CH₂)₃-S(O)(Me)- | -CH₂-CF₃ (with F) | C—F | ¹H NMR (400 MHz, DMSO-d₆) δ ppm 2.00 (m, J = 6.53 Hz, 2 H) 2.99 (s, 3 H) 3.12-3.23 (m, 2 H) 4.42 (t, J = 7.15 Hz, 2 H) 4.86 (q, J = 8.70 Hz, 2 H) 5.38 (s, 2 H) 6.55 (s, 1 H) 6.99 (t, J = 8.91 Hz, 1 H) 7.29 (d, J = 8.03 Hz, 1 H) 7.37 (dd, J = 7.91, 4.39 Hz, 1 H) 7.53 (d, J = 5.52 Hz, 1 H) 8.22 (d, J = 5.52 Hz, 1 H) 8.76 (s, 1 H) | 0.614 | >162986 |

TABLE 2-continued

| | $X_4-R_1$ | $X_5-R_1$ | $X_6-R_1$ | $R_2$ | $R_3$ | $R_4$ | $Y_7-R_5$ | $^1H$ NMR | WT activity $EC_{50}$ (nM) | SI $CC_{50}/EC_{50}$ |
|---|---|---|---|---|---|---|---|---|---|---|
| P32 | N | Cl | CH | H | 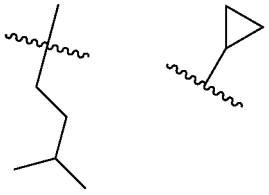 | 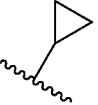 | N | $^1H$ NMR (400 MHz, DMSO-$d_6$) δ ppm 0.88 (d, J = 6.53 Hz, 6 H) 0.90-0.96 (m, 2 H) 1.05-1.12 (m, 2 H) 1.27-1.37 (m, 2 H) 1.59 (dquin, J = 13.30, 6.65, 6.65, 6.65, 6.65 Hz, 1 H) 2.98 (tt, J = 7.03, 3.51 Hz, 1 H) 4.26 (t, J = 8.00 Hz, 2 H) 5.33 (s, 2 H) 6.70 (s, 1 H) 7.17 (d, J = 8.78 Hz, 1 H) 7.29 (dd, J = 5.27, 0.75 Hz, 1 H) 7.92 (dd, J = 8.53, 0.75 Hz, 1 H) 8.25 (d, J = 5.27 Hz, 1 H) 8.37 (d, J = 0.50 Hz, 1 H) | 7.771 | >1286 |
| P33 | N | Cl | CH | H | 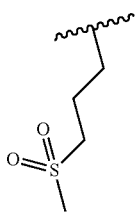 [SMILES: *CCCS(C)(=O)=O] | 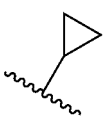 [SMILES: *C1CC1] | N | $^1H$ NMR (400 MHz, DMSO-$d_6$) δ ppm 0.90-0.98 (m, 2 H) 1.02-1.10 (m, 2 H) 1.95 (m, J = 7.40, 7.40 Hz, 2 H) 2.96 (s, 3 H) 3.00 (tt, J = 7.00, 3.80 Hz, 1 H) 3.08-3.19 (m, 2 H) 4.42 (t, J = 7.40 Hz, 2 H) 5.36 (s, 2 H) 6.64 (s, 1 H) 7.22 (d, J = 8.53 Hz, 1 H) 7.28 (d, J = 5.27 Hz, 1 H) 8.03 (d, J = 8.53 Hz, 1 H) 8.26 (d, J = 5.27 Hz, 1 H) 8.41 (s, 1 H) | 5.756 | >17372 |
| P34 | N | Cl | CH | H |  | 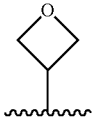 [SMILES: *C1COC1] | N | $^1H$ NMR (400 MHz, DMSO-$d_6$) δ ppm 0.88 (d, J = 6.53 Hz, 6 H) 1.26-1.40 (m, 2 H) 1.60 (dquin, J = 13.25, 6.73, 6.73, 6.73, 6.73 Hz, 1 H) 4.28 (t, J = 7.78 Hz, 2 H) 4.97 (t, J = 7.50 Hz, 2 H) 5.08 (t, J = 6.53 Hz, 2 H) 5.38 (s, 2 H) 5.52-5.63 (m, 1 H) 6.71 (s, 1 H) 7.18 (d, J = 8.53 Hz, 1 H) 7.54 (d, J = 5.27 Hz, 1 H) 7.93 (d, J = 8.53 Hz, 1 H) 8.30 (d, J = 5.27 Hz, 1 H) 8.46 (s, 1 H) | 35.012 | >2856 |
| P35 | N | Cl | CH | H | 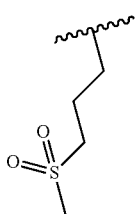 | 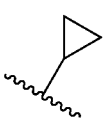 | C—H | $^1H$ NMR (400 MHz, CHLOROFORM-d) δ ppm 0.99-1.06 (m, 2 H), 1.11-1.18 (m, 2 H), 2.06-2.20 (m, 2 H), 2.86 (s, 3 H), 2.89-2.96 (m, 1 H), 3.01 (t, J = 7.4 Hz, 2 H), 4.42-4.54 (m, 2 H), 5.24 (s, 2 H), 6.79 (s, 1 H), 7.01-7.09 (m, 1 H), 7.10-7.16 (m, 3 H), 7.20-7.25 (m, 1 H), 7.61 (dd, J = 8.7, 0.6 Hz, 1 H) | 7.864 | >12716 |
| P36 | N | Cl | CH | H | 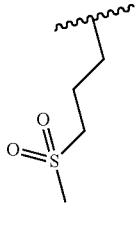 [SMILES: *CCCS(C)(=O)=O] | 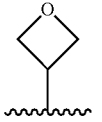 | N | $^1H$ NMR (400 MHz, DMSO-$d_6$) δ ppm 1.87-2.04 (m, 2 H), 2.96 (s, 3 H), 3.06-3.20 (m, 2 H), 4.34-4.51 (m, 2 H), 4.96 (m, J = 7.5 Hz, 2 H), 5.08 (t, J = 6.7 Hz, 2 H), 5.41 (s, 2 H), 5.51-5.64 (m, 1 H), 6.69 (s, 1 H), 7.22 (d, J = 8.5 Hz, 1 H), 7.55 (d, J = 5.3 Hz, 1 H), 8.04 (d, J = 8.5 Hz, 1 H), 8.31 (d, J = 5.3 Hz, 1 H), 8.51 (s, 1 H) | 6.814 | >14674 |
| P37 | N | Cl | CH | H | 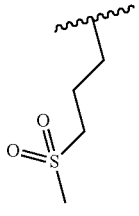 | 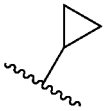 [SMILES: *C1CC1] | C—F | $^1H$ NMR (400 MHz, DMSO-$d_6$) δ ppm 0.85-0.96 (m, 2 H), 0.99-1.12 (m, 2 H), 1.84-2.06 (m, 2 H), 2.88-3.03 (m, 1 H), 2.95 (s, 3 H), 3.07-3.20 (m, 2 H), 4.43 (t, J = 7.5 Hz, 2 H), 5.30 (s, 2 H), 6.58 (s, 1 H), 6.85-7.01 (m, 1 H), 7.13-7.31 (m, 3 H), 8.03 (d, J = 8.5 Hz, 1 H) | 22.323 | >4479 |

TABLE 2-continued

| | $X_4$—$R_1$ | $X_5$—$R_1$ | $X_6$—$R_1$ | $R_2$ | $R_3$ | $R_4$ | $Y_7$—$R_5$ | $^1$H NMR | WT activity $EC_{50}$ (nM) | SI $CC_{50}$/$EC_{50}$ |
|---|---|---|---|---|---|---|---|---|---|---|
| P38 | N | Cl | CH | H | | | C—F | $^1$H NMR (400 MHz, DMSO-$d_6$) δ ppm 0.83-0.94 (m, 8 H) 1.01-1.13 (m, 2 H) 1.23-1.37 (m, 2 H) 1.59 (tt, J = 13.20, 6.70 Hz, 1 H) 2.93 (tt, J = 6.90, 3.51 Hz, 1 H) 4.27 (t, J = 8.00 Hz, 2 H) 5.28 (s, 2 H) 6.64 (s, 1 H) 6.88-6.95 (m, 1 H) 7.14 (dd, J = 9.16, 2.64 Hz, 1 H) 7.17 (d, J = 8.78 Hz, 1 H) 7.22 (dd, J = 8.66, 4.64 Hz, 1 H) 7.91 (d, J = 8.53 Hz, 1 H) | 32.84 | 1510 |
| P39 | N | Cl | CH | H | | | C—H | $^1$H NMR (400 MHz, DMSO-$d_6$) δ ppm 0.87 (d, J = 6.78 Hz, 6 H) 0.89-0.95 (m, 2 H) 1.04-1.09 (m, 2 H) 1.20-1.34 (m, 2 H) 1.58 (dquin, J = 13.24, 6.67, 6.67, 6.67, 6.67 Hz, 1 H) 2.93 (tt, J = 6.90, 3.64 Hz, 1 H) 4.26 (t, J = 8.30 Hz, 2 H) 5.29 (s, 2 H) 6.62 (s, 1 H) 7.01 (td, J = 7.80, 1.00 Hz, 1 H) 7.08 (td, J = 7.65, 1.00 Hz, 1 H) 7.13-7.20 (m, 2 H) 7.25 (d, J = 7.28 Hz, 1 H) 7.90 (d, J = 8.78 Hz, 1 H) | 128.76 | >388 |
| P40 | N | Cl | CH | H | | | N | $^1$H NMR (400 MHz, DMSO-$d_6$) δ ppm 0.88-0.96 (m, 2 H) 1.04-1.14 (m, 2 H) 1.65-1.79 (m, 2 H) 2.21-2.37 (m, 2 H) 2.97 (tt, J = 6.96, 3.58 Hz, 1 H) 4.36 (t, J = 7.65 Hz, 2 H) 5.35 (s, 2 H) 6.68 (s, 1 H) 7.21 (d, J = 8.53 Hz, 1 H) 7.29 (d, J = 5.27 Hz, 1 H) 8.05 (d, J = 8.78 Hz, 1 H) 8.26 (d, J = 5.27 Hz, 1 H) 8.41 (s, 1 H) | 2.699 | >37045 |
| P42 | N | Cl | CH | H | | | N | $^1$H NMR (400 MHz, DMSO-$d_6$) δ ppm 0.88-0.96 (m, 2 H) 1.03-1.12 (m, 2 H) 1.47-1.72 (m, 4 H) 2.98 (tt, J = 6.93, 3.61 Hz, 1 H) 4.18-4.53 (m, 4 H) 5.34 (s, 2 H) 6.69 (s, 1 H) 7.18 (d, J = 8.53 Hz, 1 H) 7.28 (d, J = 5.02 Hz, 1 H) 8.01 (d, J = 8.53 Hz, 1 H) 8.25 (d, J = 5.27 Hz, 1 H) 8.39 (s, 1 H) | 2.839 | 17031 |
| P43 | N | Cl | CH | H | | | C—H | $^1$H NMR (400 MHz, DMSO-$d_6$) δ ppm 0.83-0.96 (m, 2 H) 1.06 (m, J = 5.27 Hz, 2 H) 1.58-1.77 (m, 2 H) 2.27 (m, J = 4.52 Hz, 2 H) 2.86-2.98 (m, 1 H) 4.37 (t, J = 6.78 Hz, 2 H) 5.31 (s, 2 H) 6.62 (s, 1 H) 6.95-7.36 (m, 5 H) 8.04 (d, J = 8.28 Hz, 1 H) | 69.218 | 1291 |
| P45 | N | CH | CH | H | | | N | $^1$H NMR (400 MHz, DMSO-$d_6$) δ ppm 0.88-0.97 (m, 2 H) 1.03-1.14 (m, 2 H) 1.47-1.75 (m, 4 H) 2.99 (tt, J = 6.90, 3.64 Hz, 1 H) 4.22-4.55 (m, 4 H) 5.34 (s, 2 H) 6.70 (s, 1 H) 7.13 (dd, J = 8.28, 4.52 Hz, 1 H) 7.28 (d, J = 5.27 Hz, 1 H) 7.89 (d, J = 8.03 Hz, 1 H) 8.24 (d, J = 5.27 Hz, 1 H) 8.31 (dd, J = 4.52, 1.26 Hz, 1 H) 8.40 (s, 1 H) | 42.875 | >2332 |
| P46 | N | $CF_3$ | CH | H | | | N | $^1$H NMR (400 MHz, DMSO-$d_6$) δ ppm 0.89-0.98 (m, 2 H) 1.04-1.14 (m, 2 H) 1.52-1.77 (m, 4 H) 2.99 (tt, J = 6.90, 3.51 Hz, 1 H) 4.30-4.54 (m, 4 H) 5.40 (s, 2 H) 6.85 (s, 1 H) 7.29 (d, J = 5.02 Hz, 1 H) 7.61 (d, J = 8.53 Hz, 1 H) 8.18 (d, J = 8.53 Hz, 1 H) 8.26 (d, J = 5.27 Hz, 1 H) 8.41 (s, 1 H) | 132 | >755 |

TABLE 2-continued

| | $X_4$—$R_1$ | $X_5$—$R_1$ | $X_6$—$R_1$ | $R_2$ | $R_3$ | $R_4$ | $Y_7$—$R_5$ | $^1$H NMR | WT activity $EC_{50}$ (nM) | SI $CC_{50}$/$EC_{50}$ |
|---|---|---|---|---|---|---|---|---|---|---|
| P47 | N | Cl | CH | H | 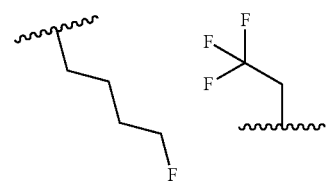 | 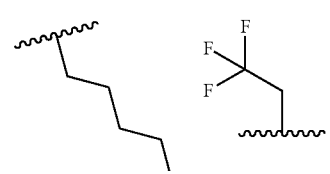 | C—F | $^1$H NMR (400 MHz, DMSO-$d_6$) δ ppm 1.50-1.76 (m, 4 H), 4.34 (d, J = 2.3 Hz, 3 H), 4.46 (t, J = 5.6 Hz, 1 H), 4.86 (q, J = 9.2 Hz, 2 H), 5.38 (s, 2 H), 6.59 (s, 1 H), 6.93-7.05 (m, 1 H), 7.19 (d, J = 8.5 Hz, 1 H), 7.27 (dd, J = 9.0, 2.3 Hz, 1 H), 7.36 (dd, J = 8.8, 4.5 Hz, 1 H), 8.01 (d, J = 8.5 Hz, 1 H) | 138 | >720 |
| P48 | N | Cl | CH | H | 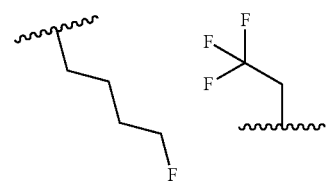 | 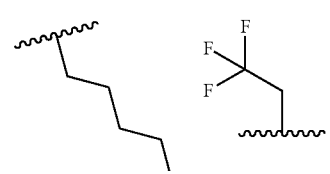 | N | $^1$H NMR (400 MHz, DMSO-$d_6$) δ ppm 1.49-1.77 (m, 4 H), 4.23-4.40 (m, 3 H), 4.46 (t, J = 5.8 Hz, 1 H), 4.91 (q, J = 9.2 Hz, 2 H), 5.45 (s, 2 H), 6.66 (s, 1 H), 7.20 (d, J = 8.8 Hz, 1 H), 7.45 (d, J = 5.3 Hz, 1 H), 8.02 (d, J = 8.5 Hz, 1 H), 8.32 (d, J = 5.3 Hz, 1H), 8.50 (s, 1 H) | 7.358 | 10490 |
| P49 | N | Cl | CH | H | 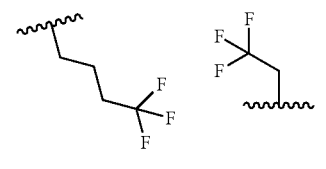 | 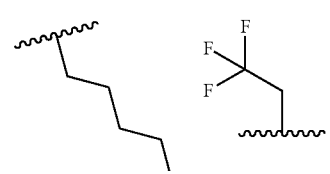 | N | $^1$H NMR (400 MHz, DMSO-$d_6$) δ ppm 1.68-1.82 (m, 2 H) 2.19-2.35 (m, 2 H) 4.37 (t, J = 7.65 Hz, 2 H) 4.90 (q, J = 9.20 Hz, 2 H) 5.45 (s, 2 H) 6.64 (s, 1 H) 7.22 (d, J = 8.78 Hz, 1 H) 7.45 (d, J = 5.27 Hz, 1 H) 8.06 (d, J = 8.78 Hz, 1 H) 8.32 (d, J = 5.27 Hz, 1 H) 8.51 (s, 1 H) | 2.095 | >34306 |
| P50 | N | Cl | CH | H | 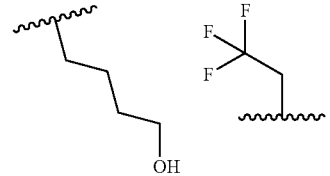 | 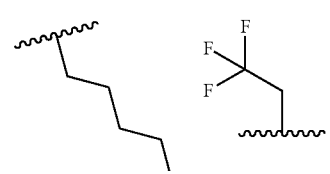 | N | | 10.108 | >4946 |
| P51 | N | Cl | CH | H | 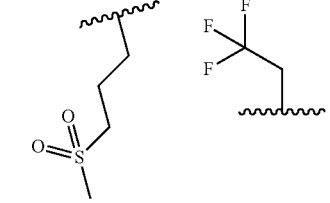 | 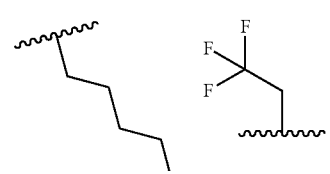 | C—H | $^1$H NMR (400 MHz, DMSO-$d_6$) δ ppm 1.95-2.07 (m, 2 H) 2.98 (s, 3 H) 3.12-3.21 (m, 2 H) 4.44 (t, J = 7.53 Hz, 2 H) 4.86 (q, J = 9.20 Hz, 2 H) 5.40 (s, 2 H) 6.50 (s, 1 H) 6.94-7.04 (m, 1 H) 7.23 (d, J = 8.53 Hz, 1 H) 7.30 (dd, J = 8.91, 2.38 Hz, 1 H) 7.38 (dd, J = 8.66, 4.39 Hz, 1 H) 8.04 (d, J = 8.53 Hz, 1 H) | 14.518 | >6887 |
| P52 | N | Cl | CH | H | 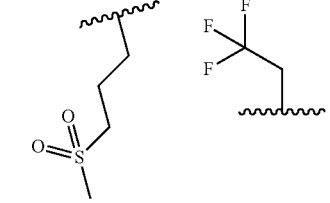 | 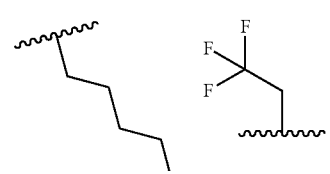 | N | $^1$H NMR (400 MHz, DMSO-$d_6$) δ ppm 1.89-2.10 (m, 2 H) 2.91-3.03 (m, 3 H) 3.09-3.22 (m, 2 H) 4.44 (t, J = 7.53 Hz, 2 H) 4.90 (q, J = 9.20 Hz, 2 H) 5.47 (s, 2 H) 6.58 (s, 1 H) 7.23 (d, J = 8.53 Hz, 1 H) 7.46 (d, J = 5.27 Hz, 1 H) 8.05 (d, J = 8.53 Hz, 1 H) 8.33 (d, J = 5.27 Hz, 1 H) 8.51 (s, 1 H) LCMS m/z = 502 (M + H)$^+$ | 0.84 | >119028 |
| P53 | N | Cl | CH | H | 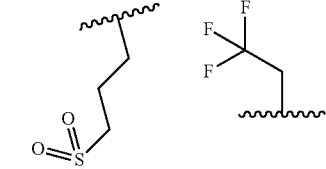 | 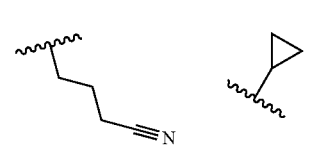 | N | $^1$H NMR (400 MHz, DMSO-$d_6$) δ ppm 0.83-1.01 (m, 2 H), 1.02-1.22 (m, 2 H), 1.78-2.08 (m, 2 H), 2.55 (t, J = 7.3 Hz, 2 H), 3.00-3.15 (m, 1 H), 4.36 (t, J = 7.2 Hz, 2 H), 5.36 (s, 2 H), 6.57 (s, 1 H), 7.20 (d, J = 8.5 Hz, 1 H), 7.29 (d, J = 5.3 Hz, 1 H), 8.02 (d, J = 8.5 Hz, 1 H), 8.26 (d, J = 5.0 Hz, 1H), 8.41 (s, 1H) | 15.849 | >6236 |

TABLE 2-continued

| | X₄—R₁ | X₅—R₁ | X₆—R₁ | R₂ | R₃ | R₄ | Y₇—R₅ | ¹H NMR | WT activity EC₅₀ (nM) | SI CC₅₀/EC₅₀ |
|---|---|---|---|---|---|---|---|---|---|---|
| P54 | N | Cl | CH | H | (butyl nitrile) | (CH₂CF₃ with extra F) | N | ¹H NMR (400 MHz, DMSO-d₆) δ ppm 1.89-2.03 (m, 2 H), 2.54 (t, J = 7.4 Hz, 2 H), 4.37 (t, J = 7.4 Hz, 2 H), 4.91 (dd, J = 9.5 Hz, 2 H), 5.46 (s, 2 H), 6.52 (s, 1 H), 7.21 (d, J = 8.5 Hz, 1 H), 7.45 (d, J = 5.3 Hz, 1 H), 8.03 (d, J = 8.8 Hz, 1 H), 8.33 (d, J = 5.3 Hz, 1H), 8.51 (s, 1 H) | | |

TABLE 3

| | structure | ¹H NMR | WT activity EC₅₀ (nM) | SI CC₅₀/EC50 |
|---|---|---|---|---|
| P24 | (structure) | ¹H NMR (360 MHz, DMSO-d₆) δ ppm 0.96 (m, J = 3.29 Hz, 2 H) 1.09 (m, J = 5.12 Hz, 2 H) 1.87 (quin, J = 7.87 Hz, 2 H) 2.33 (m, J = 5.12 Hz, 2 H) 3.04 (tt, J = 7.04, 3.57 Hz, 1 H) 4.41 (t, J = 7.50 Hz, 2 H) 5.27-5.37 (m, 2 H) 6.29-6.35 (m, 1 H) 7.34 (dd, J = 5.49, 2.20 Hz, 1 H) 7.56 (d, J = 5.85 Hz, 1 H) 7.89 (dd, J = 5.31, 1.65 Hz, 1 H) 8.21 (d, J = 1.00 Hz, 1 H) 8.71 (s, 1 H) | 0.17 | >589061 |
| P44 | (structure) | ¹H NMR (400 MHz, DMSO-d₆) δ ppm 0.94 (m, J = 2.76 Hz, 2 H) 1.06 (m, J = 5.27 Hz, 2 H) 1.52-1.79 (m, 4 H) 2.97 (tt, J = 6.84, 3.33 Hz, 1 H) 4.24-4.52 (m, 4 H) 5.33 (s, 2 H) 6.67 (s, 1 H) 7.19 (d, J = 8.53 Hz, 1 H) 7.33 (s, 1 H) 8.01 (d, J = 8.53 Hz, 1 H) 8.17 (s, 1 H) | 17.908 | 620 |

The invention claimed is:
1. A compound selected from the group consisting of:
P1
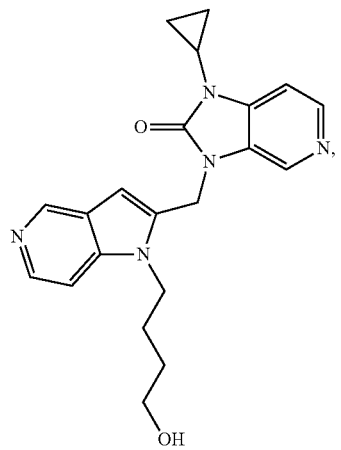
P2
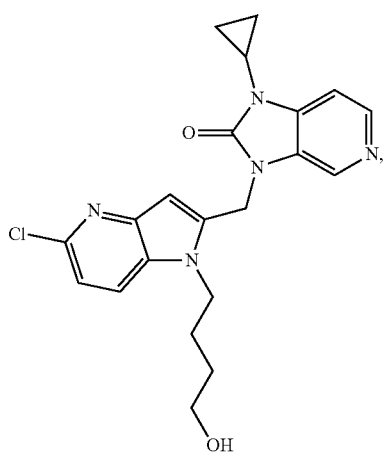
P3
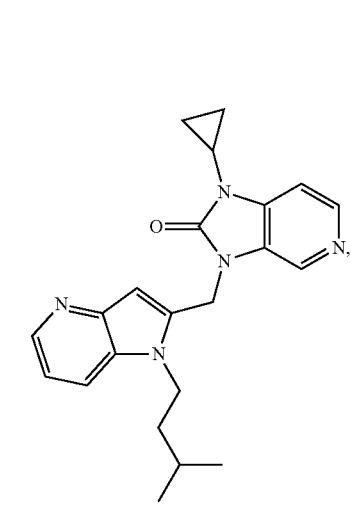
P4
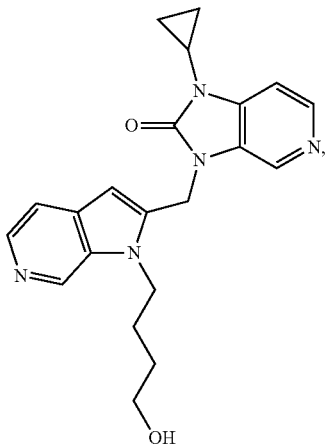
P5
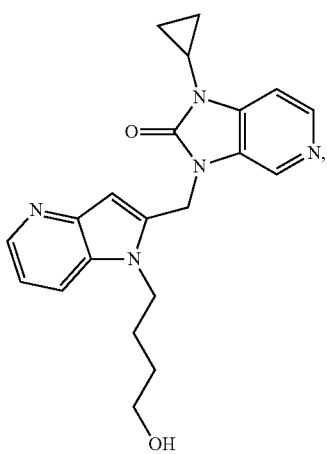
P6
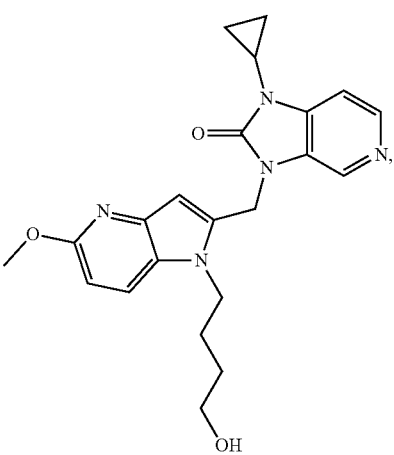

-continued
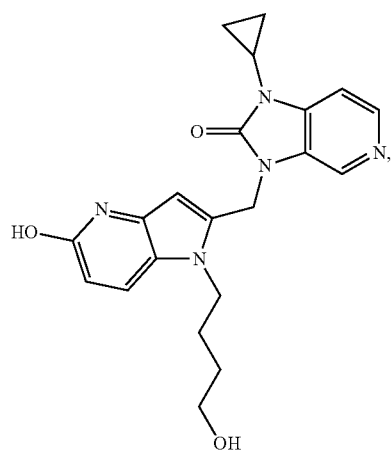
P8
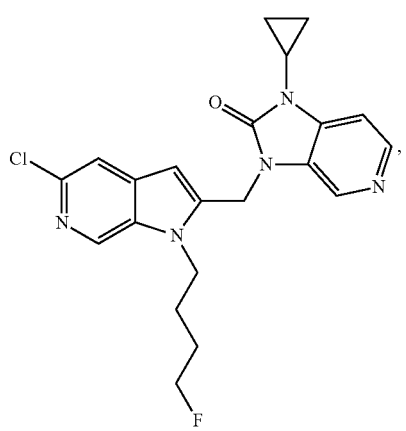
P11
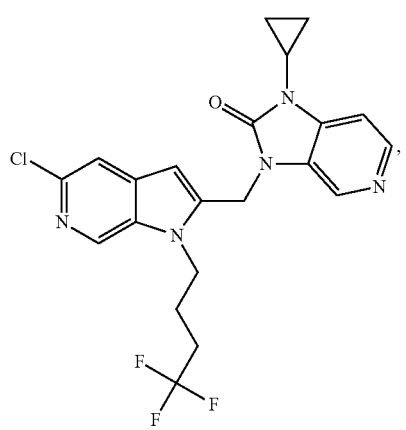
P12
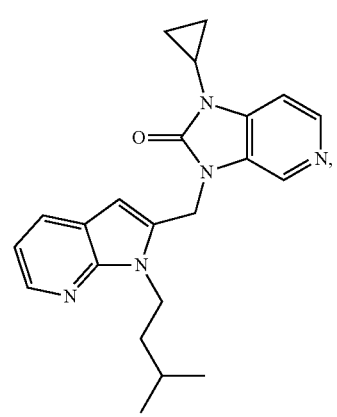
P9
P10
P13

P14
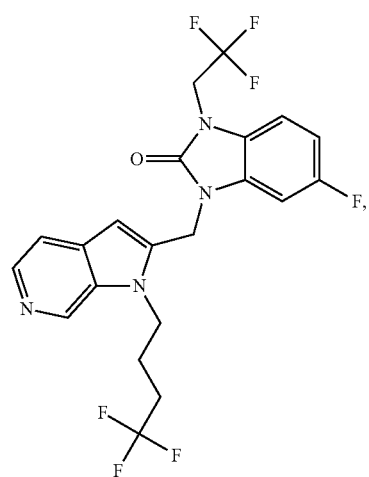
P15
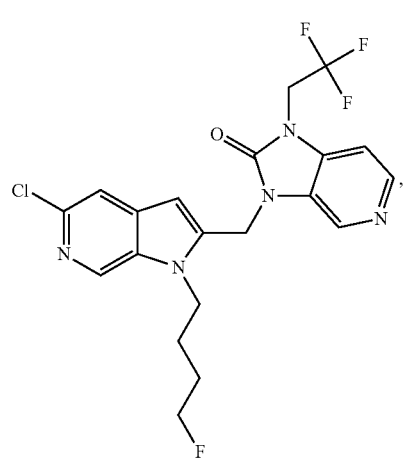
P16
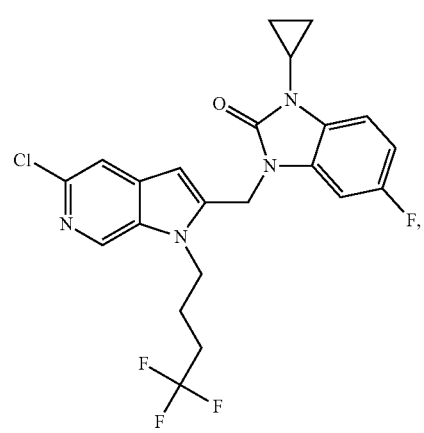
P17
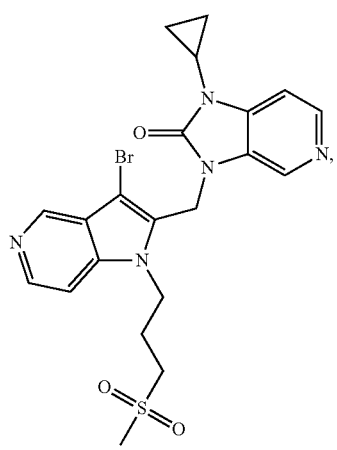
P18
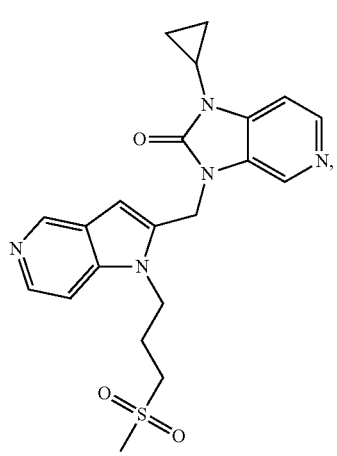
P19
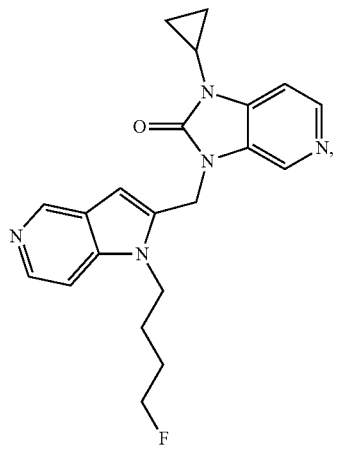

P20
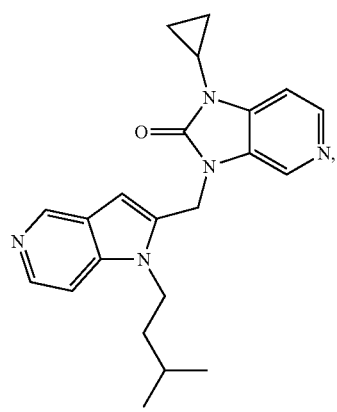
P21
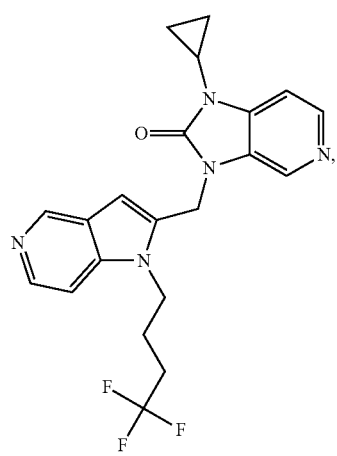
P22
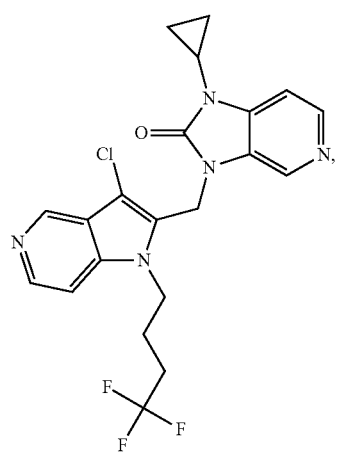
P23
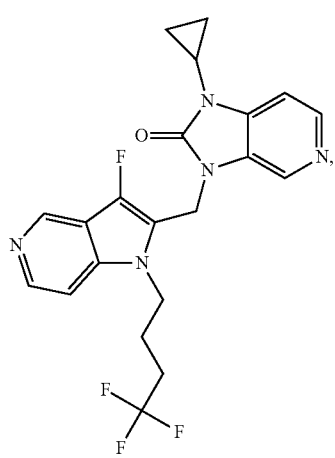
P24
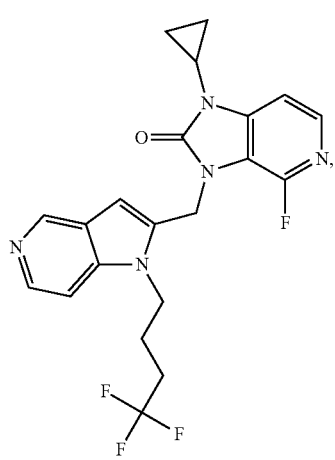
P25
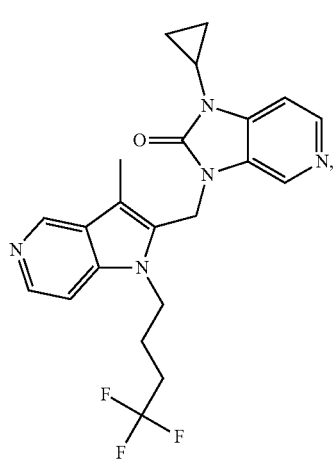

-continued
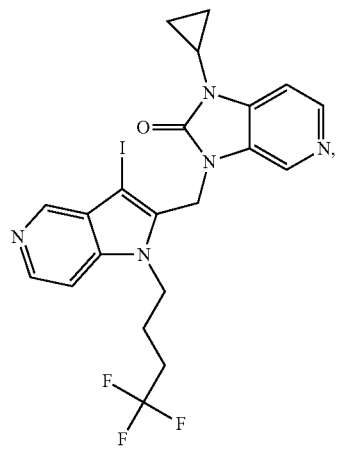
P26
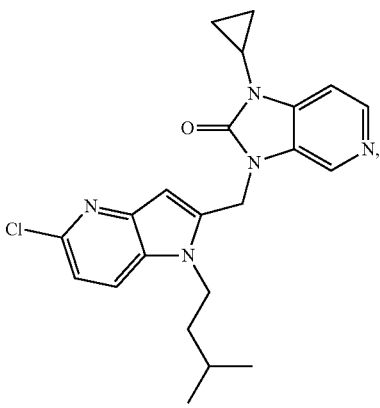
P32
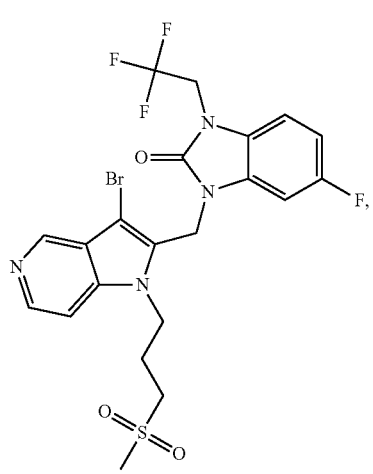
P29
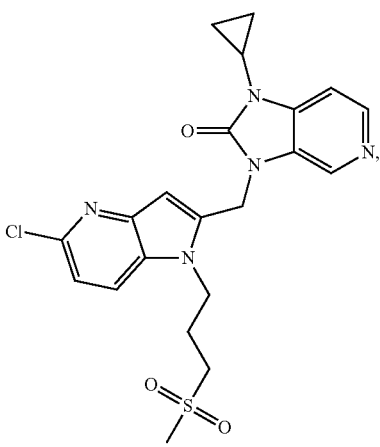
P33
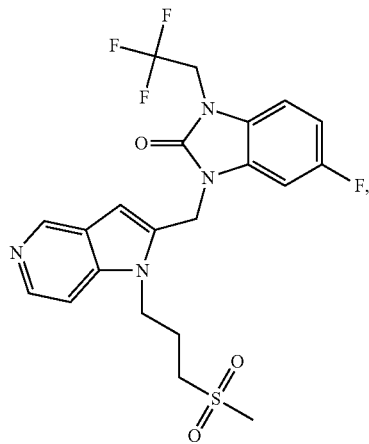
P30
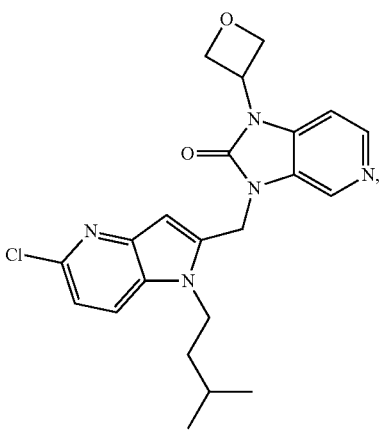
P34

P35 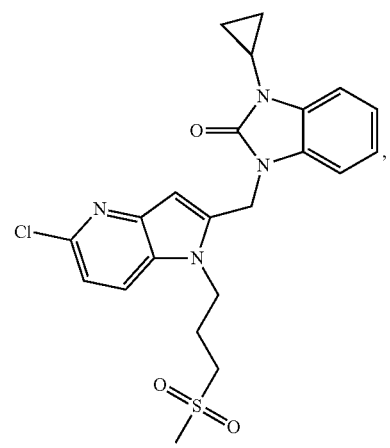
P36 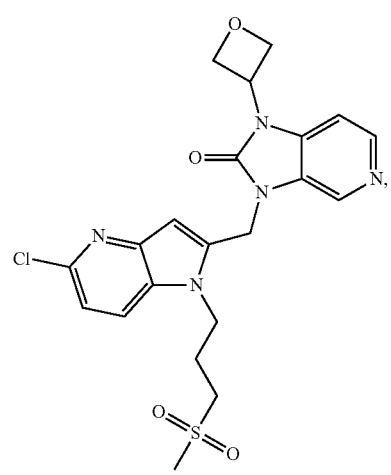
P37 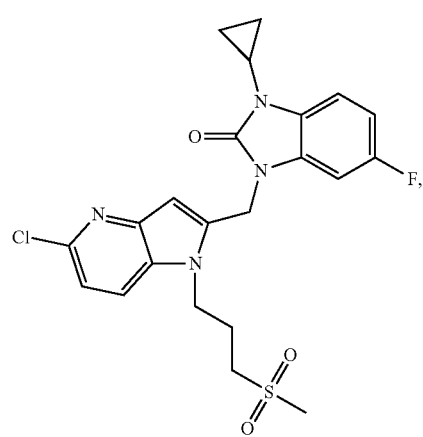
P38 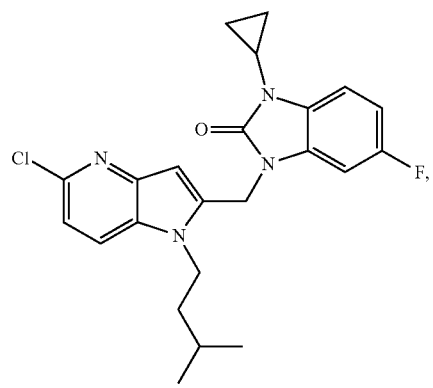
P39 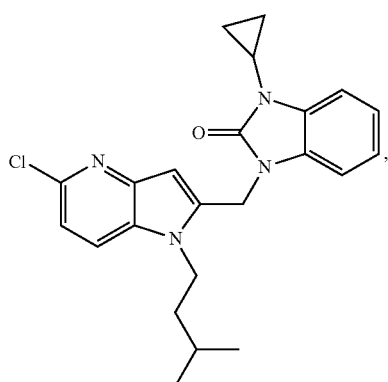
P40 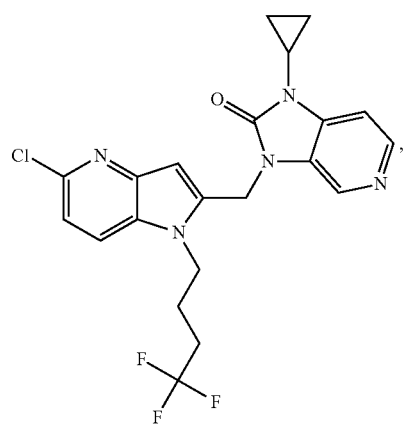
P42 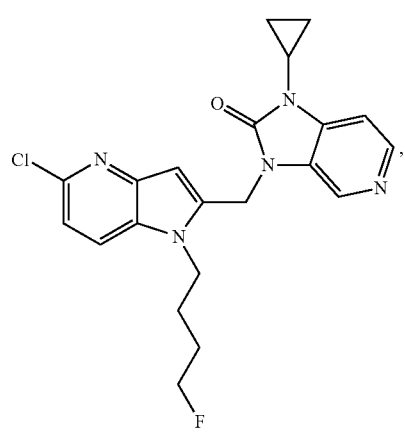

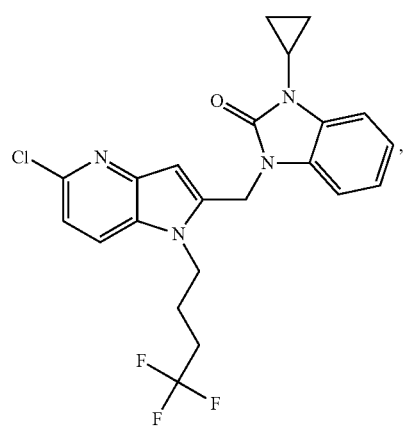
P43
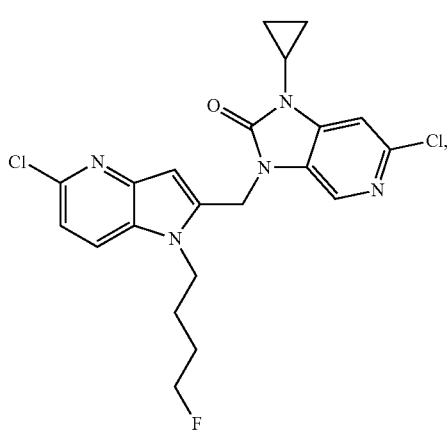
P44
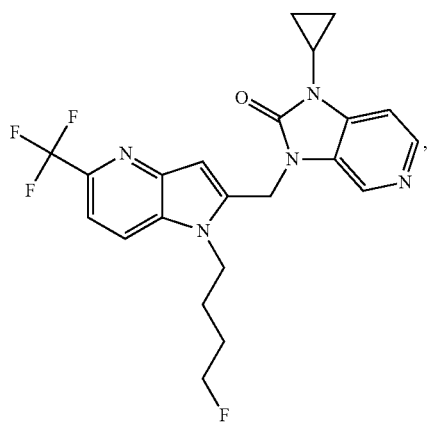
P46
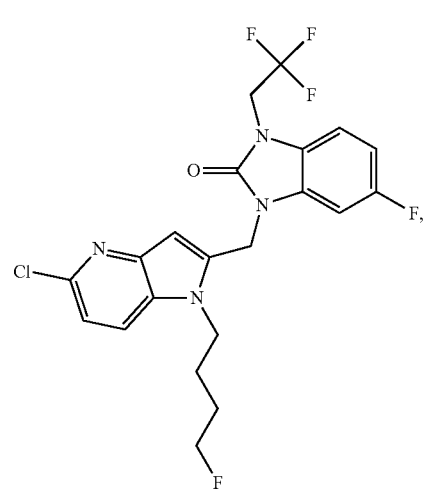
P47
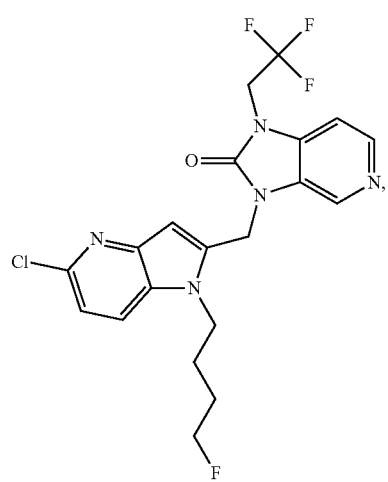
P48

P49
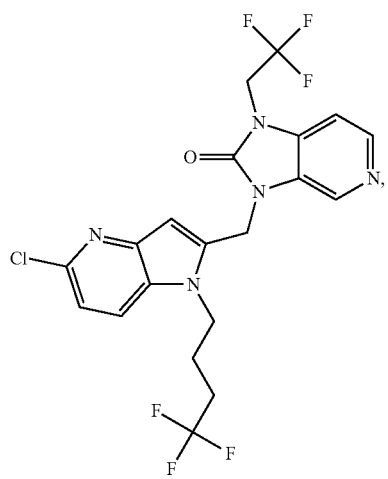
P50
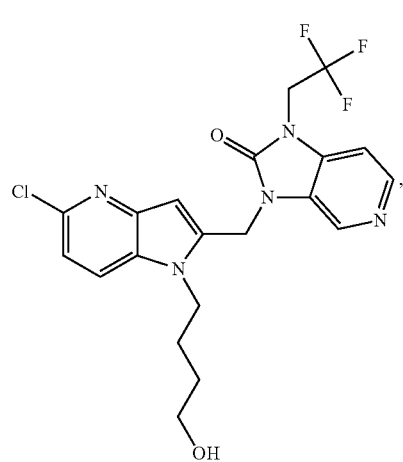
P51
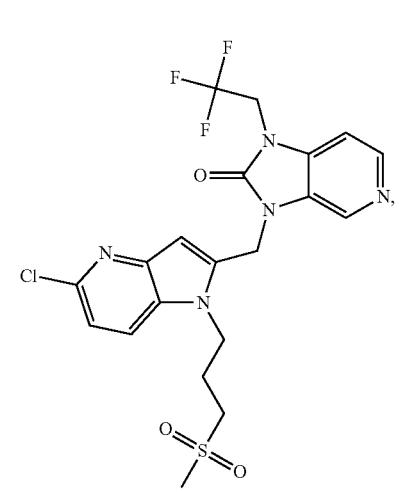
P52
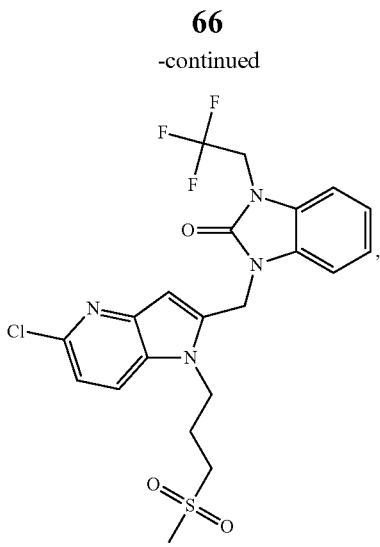
P53
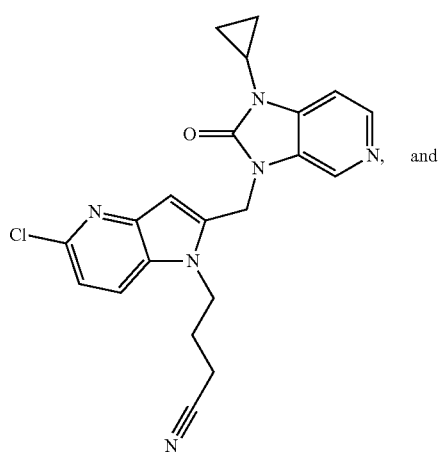
P54
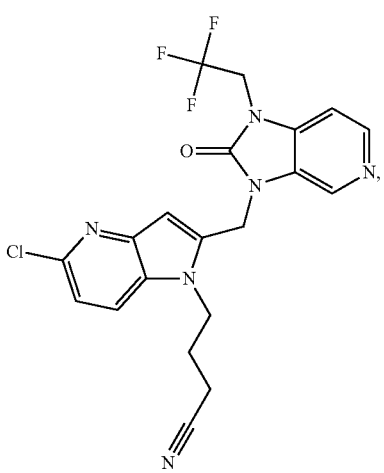
and an N-oxide, addition salt, or quaternary amine thereof.
2. A pharmaceutical composition comprising a compound selected from the group consisting of:

P1
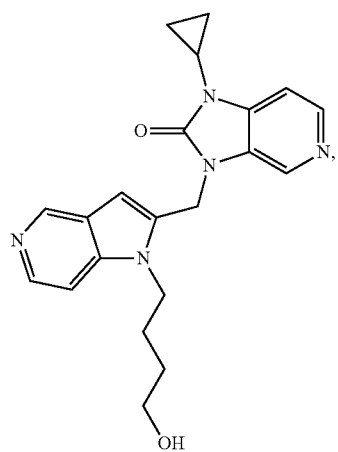
P4
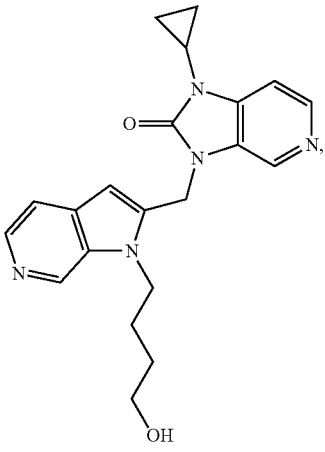
P2
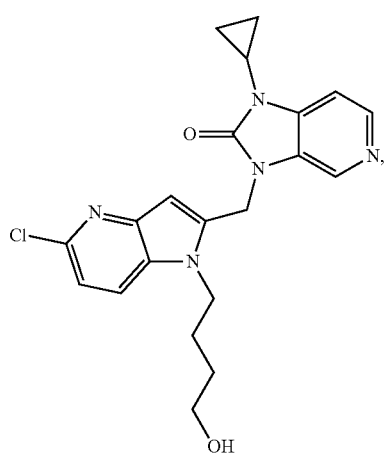
P5
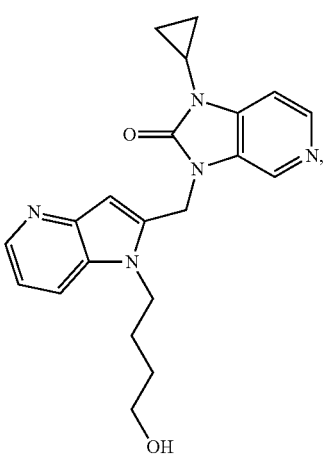
P3
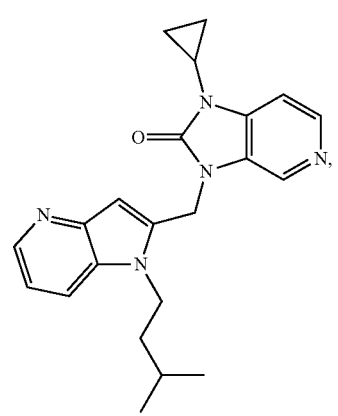
P6
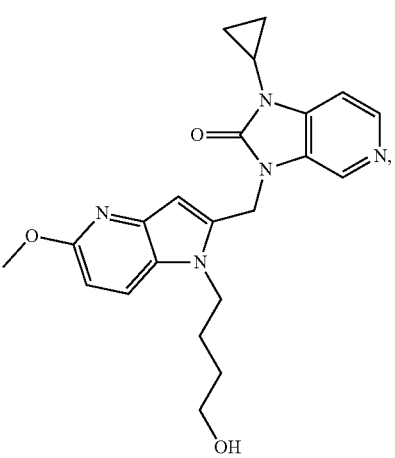

69
-continued
P8
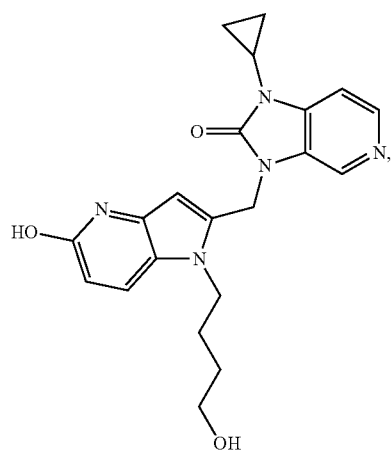
P9
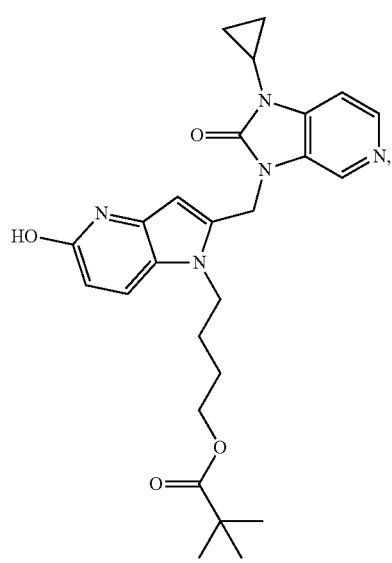
P10
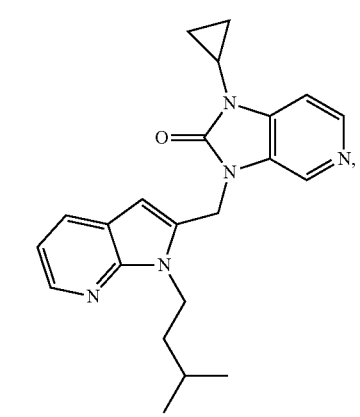
70
-continued
P11
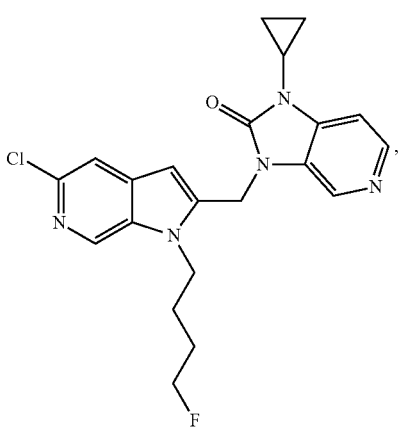
P12
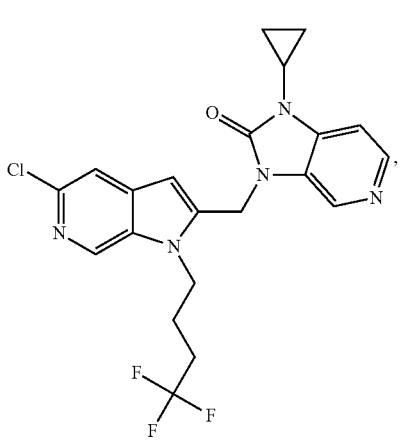
P13
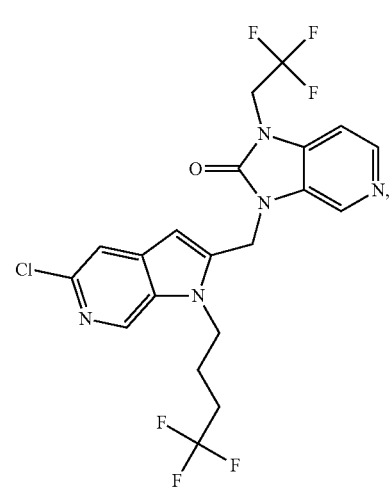

-continued
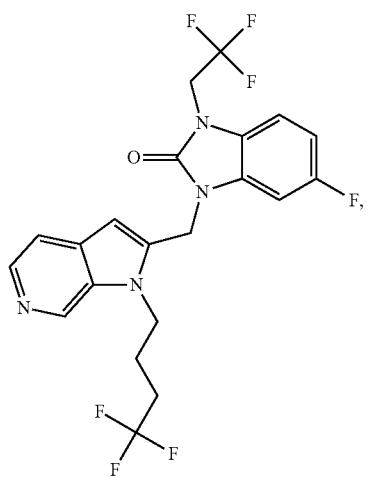
P14
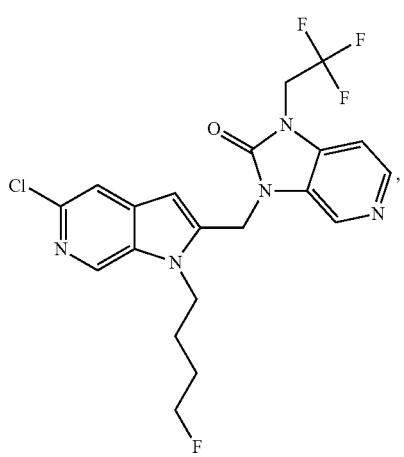
P15
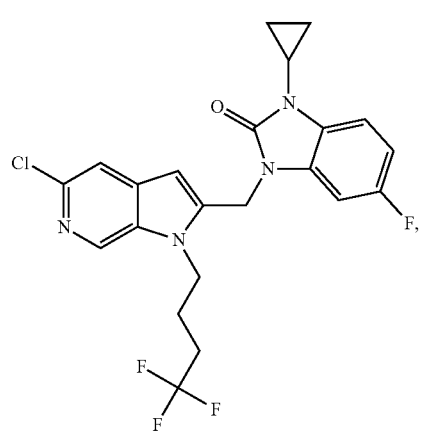
P16
-continued
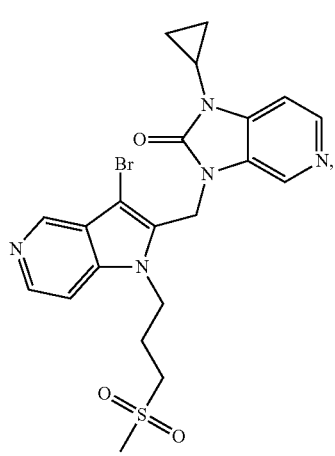
P17
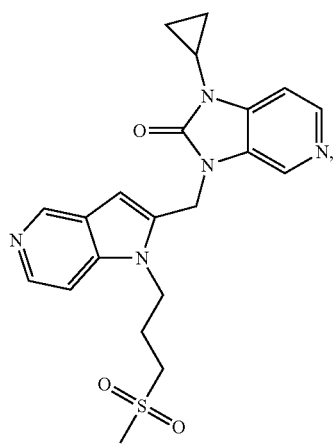
P18
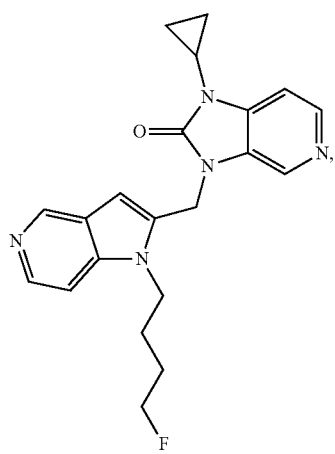
P19

P20
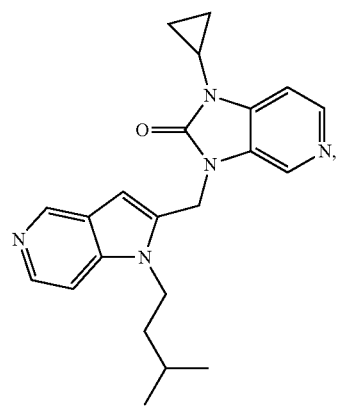
P21
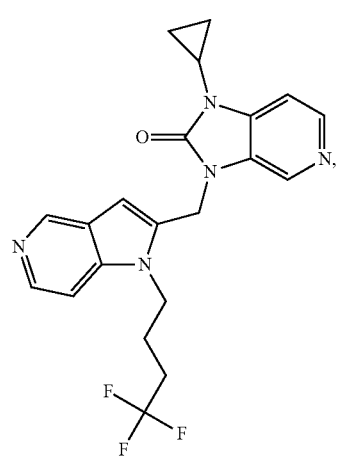
P22
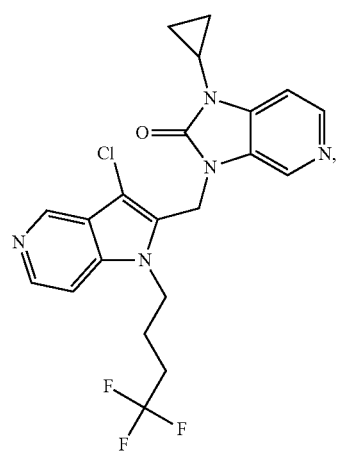
P23
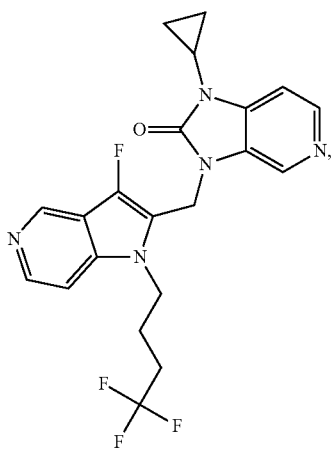
P24
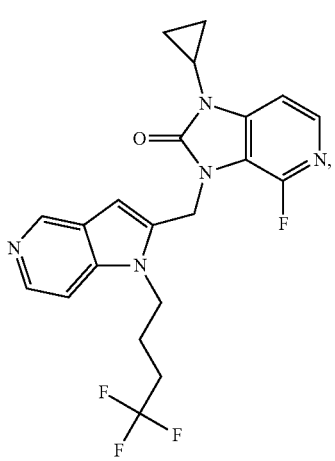
P25
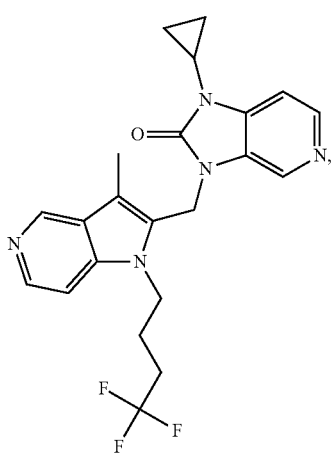

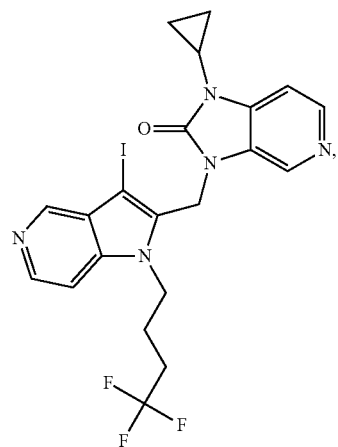 P26
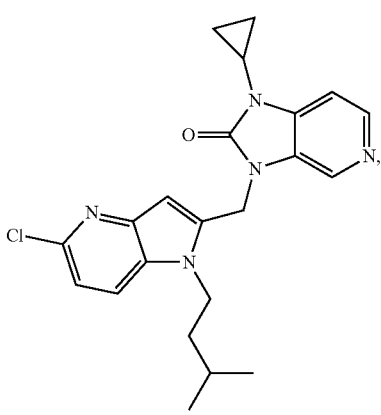 P32
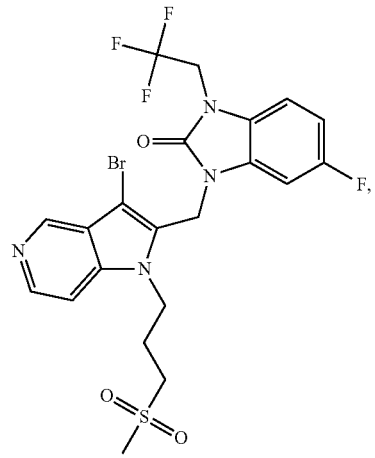 P29
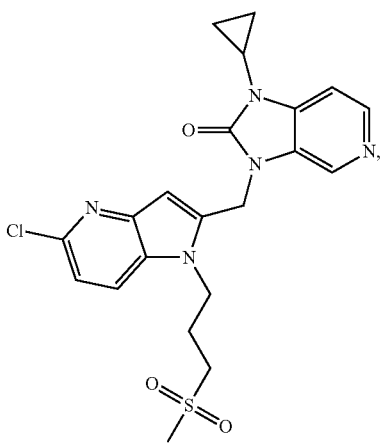 P33
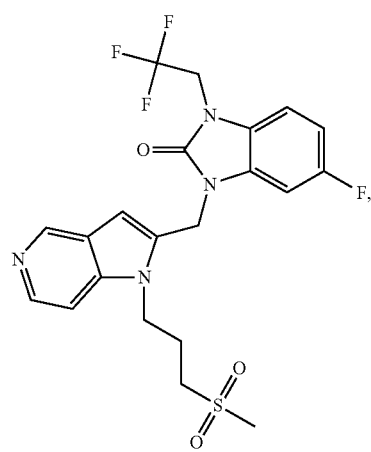 P30
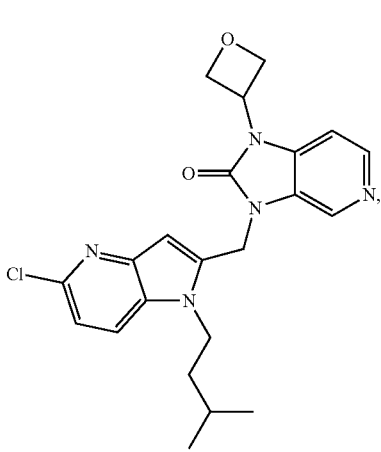 P34

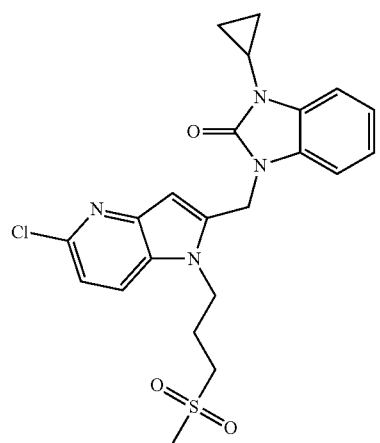 P35
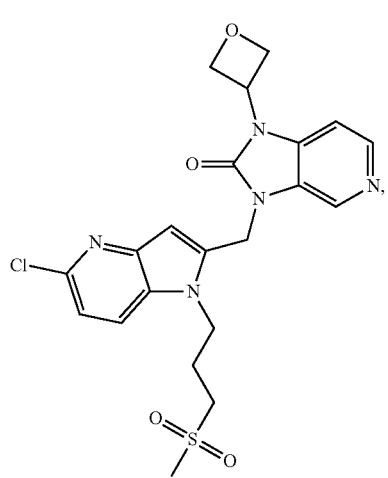 P36
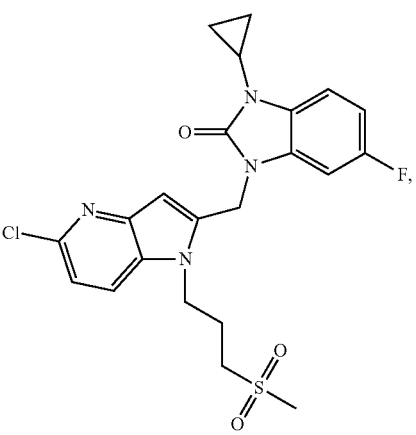 P37
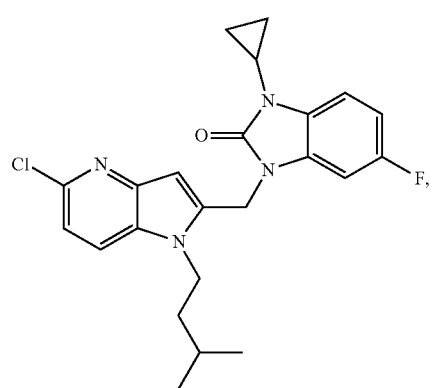 P38
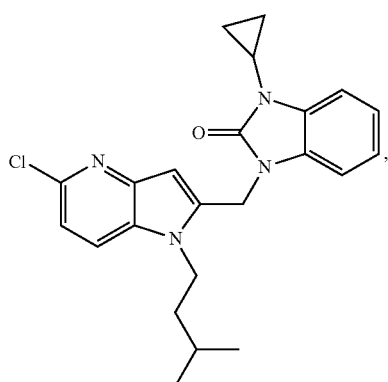 P39
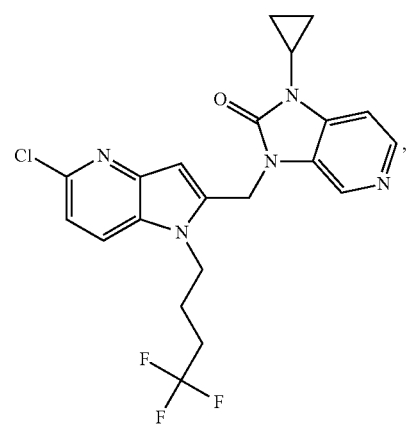 P40
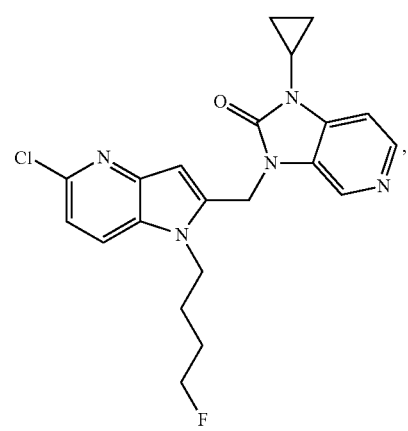 P42

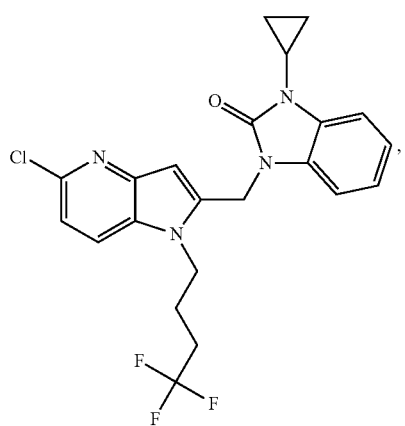
P43
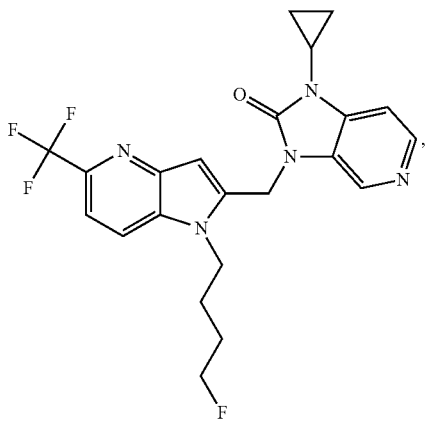
P46
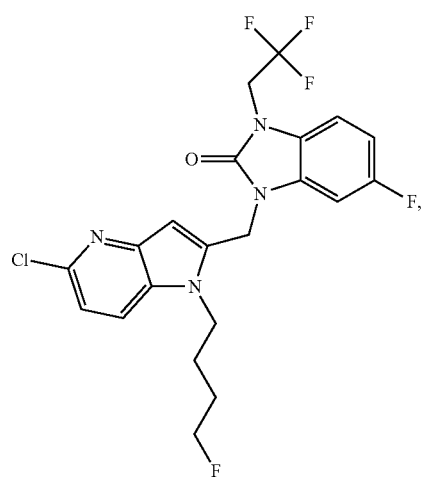
P47
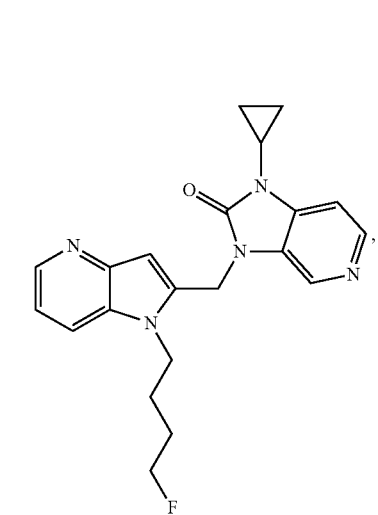
P44
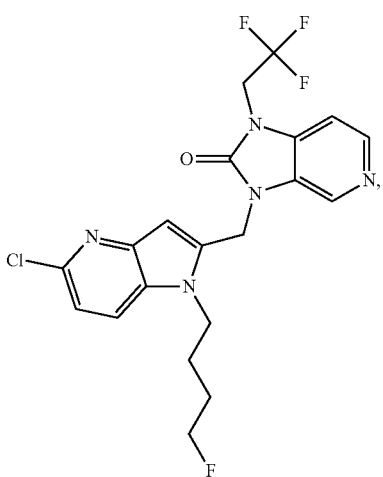
P48
P45

P49
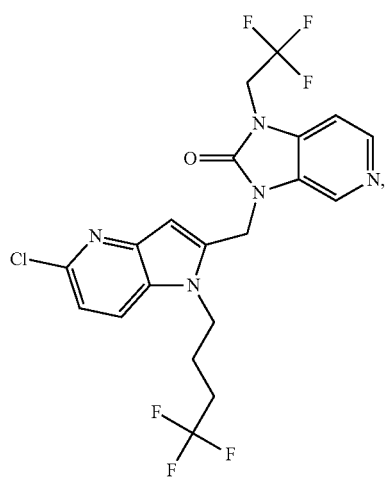
P50
P51
P52
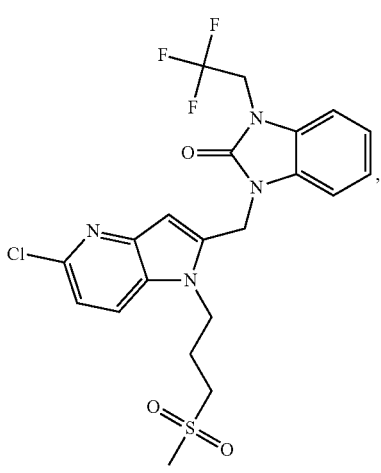
P53
P54
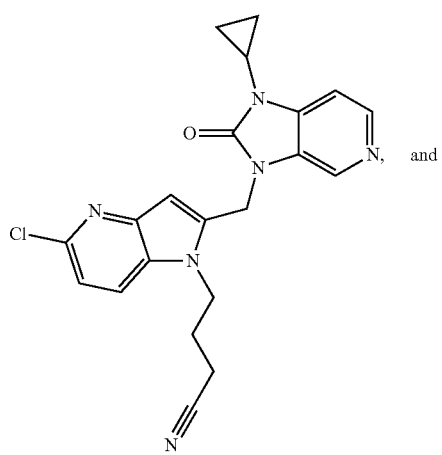
and an N-oxide, addition salt, or quaternary amine thereof.
3. A method of treating a respiratory syncytial viral (RSV) infection comprising administering to a subject in need thereof an anti-virally effective amount of a compound selected from the group consisting of:

83
P1 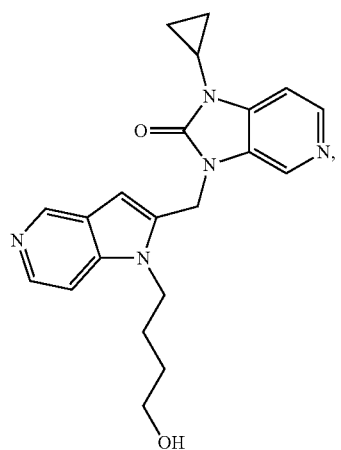
P2 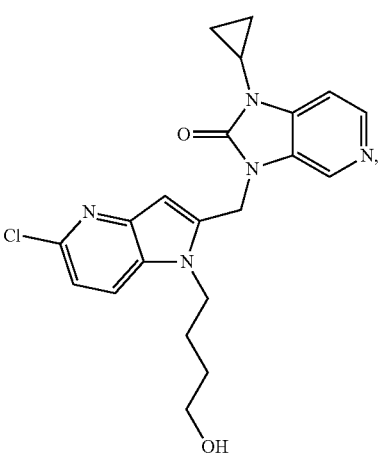
P3 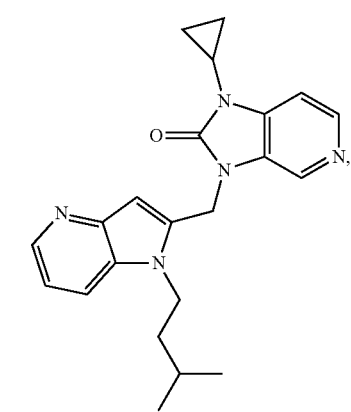
84
-continued
P4 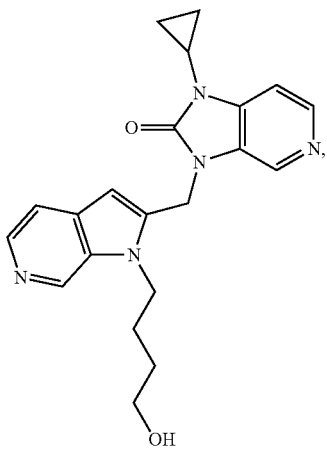
P5 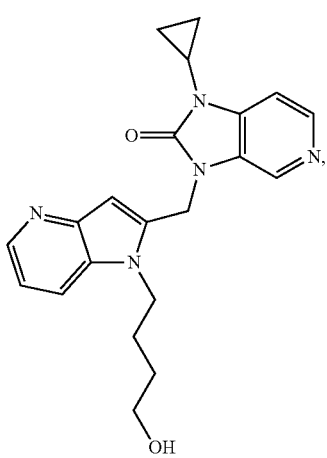
P6 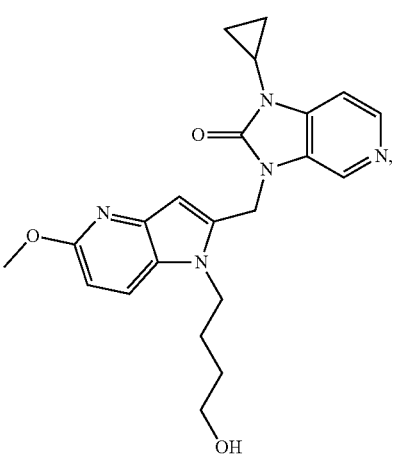

85
-continued
P8
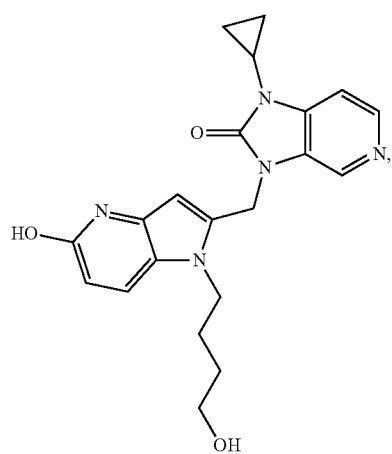
P9
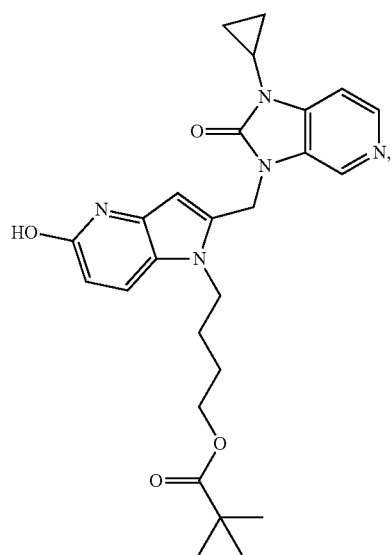
P10
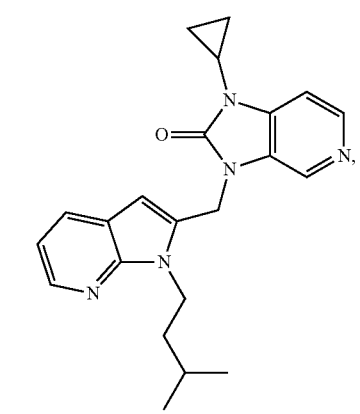
86
-continued
P11
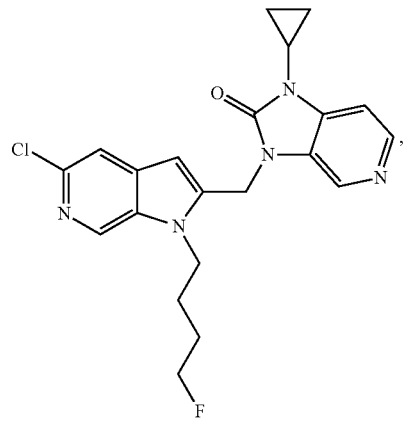
P12
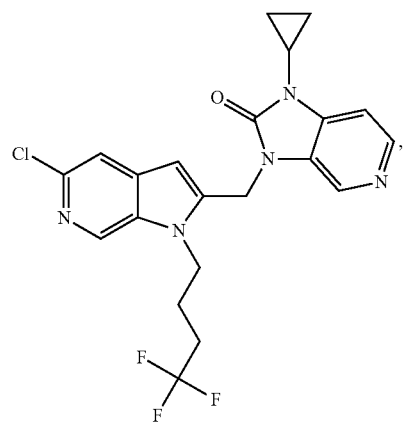
P13
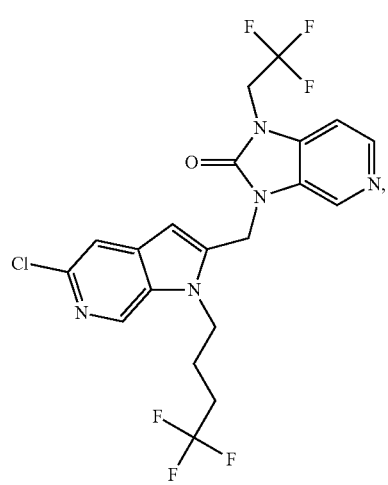

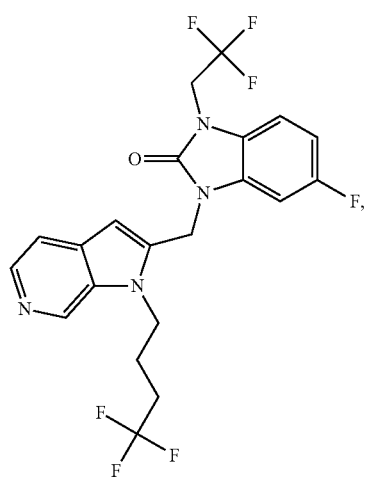 P14
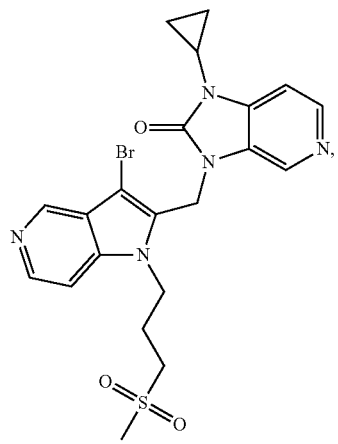 P17
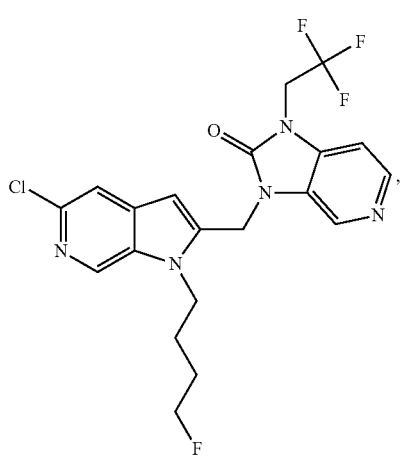 P15
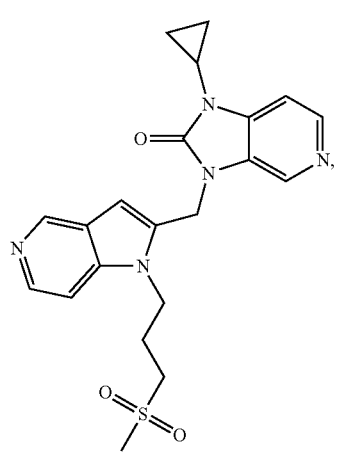 P18
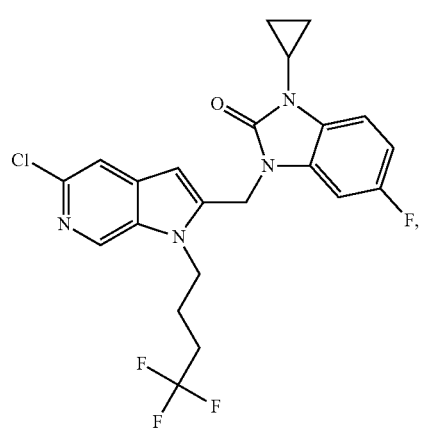 P16
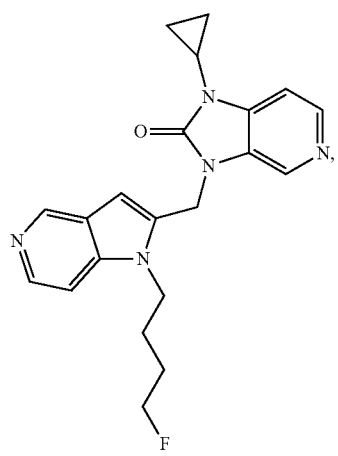 P19

P20
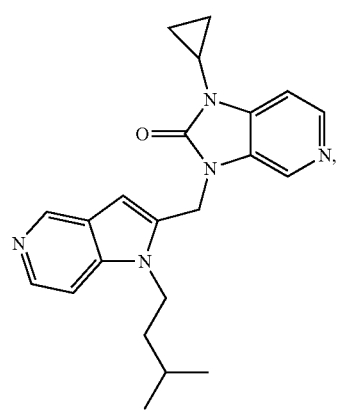
P21
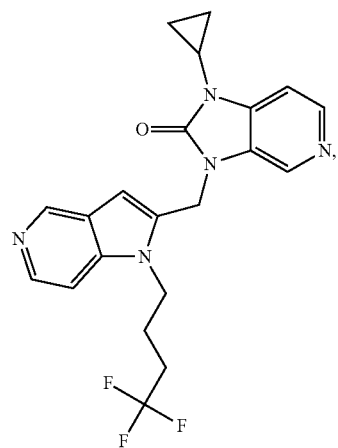
P22
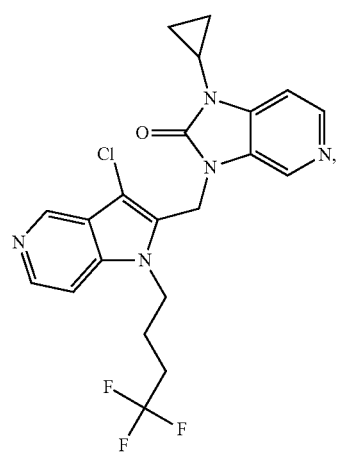
P23
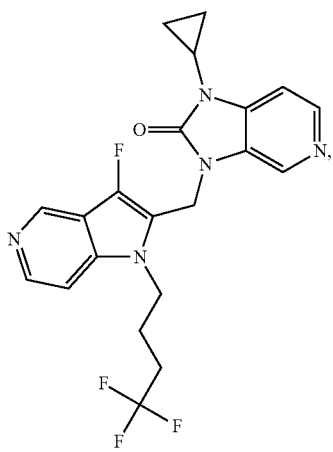
P24
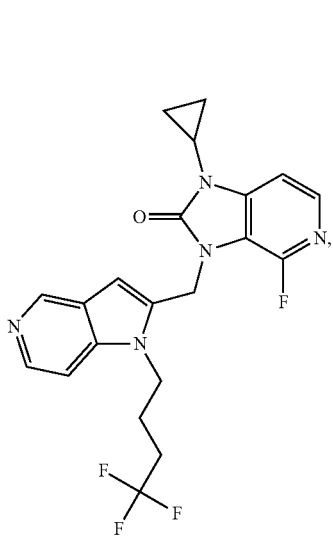
P25
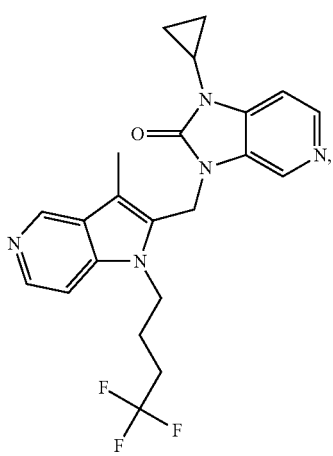

P26 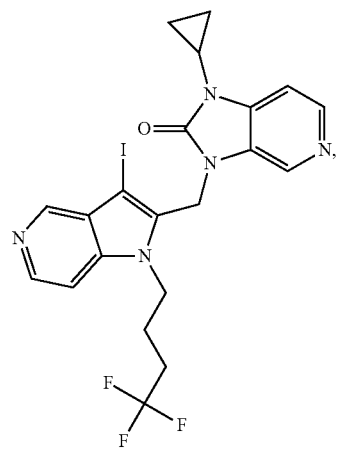
P29 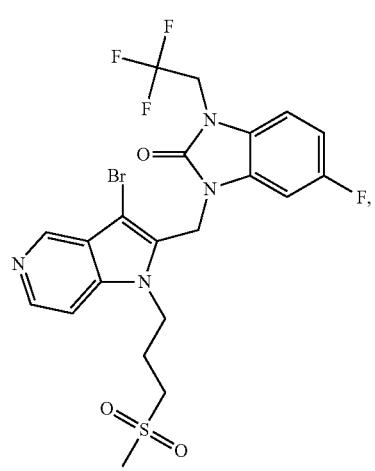
P30 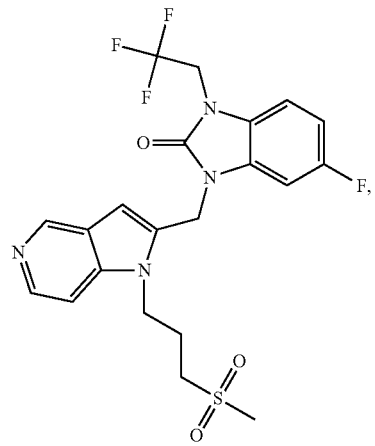
P32 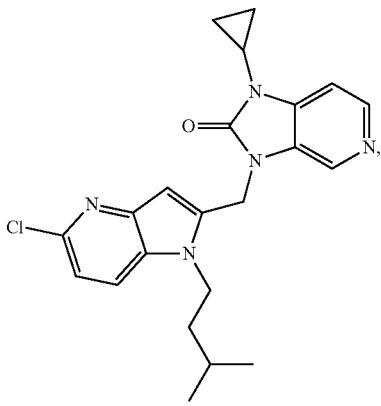
P33 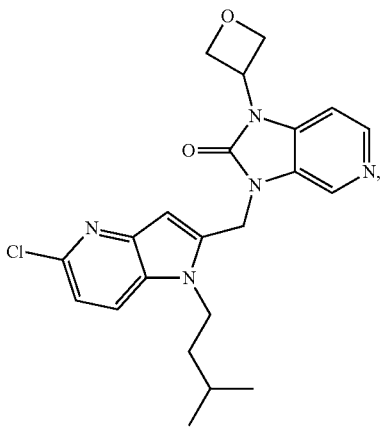
P34

P35
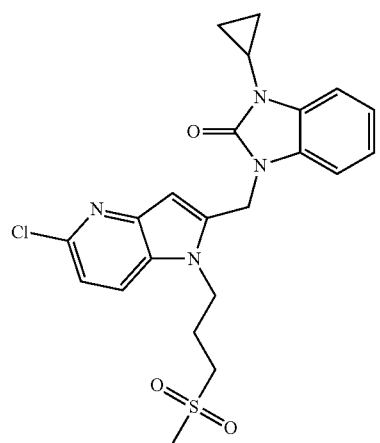
P36
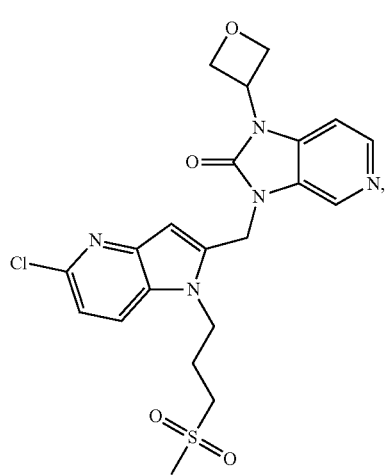
P37
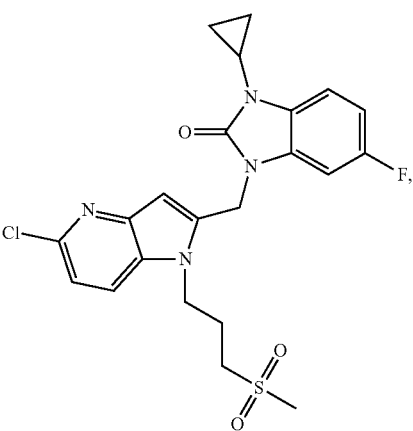
P38
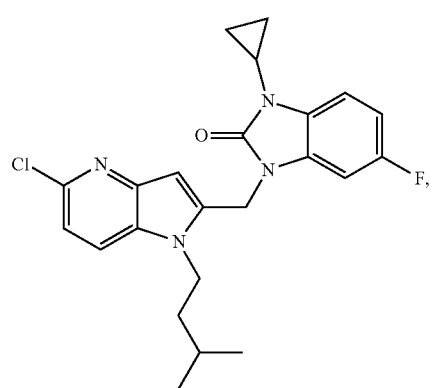
P39
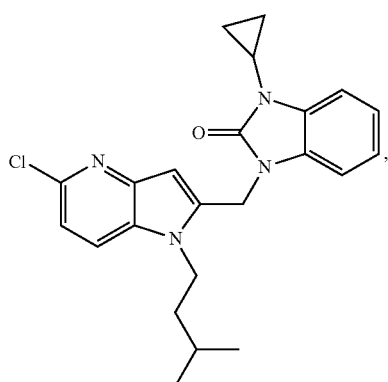
P40
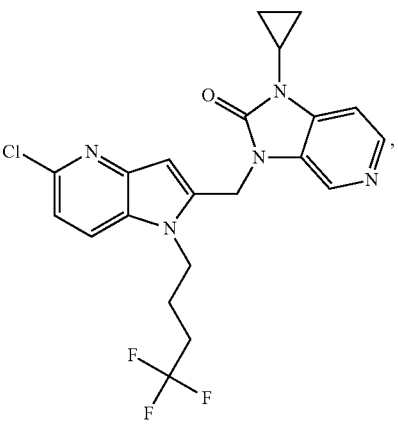
P42
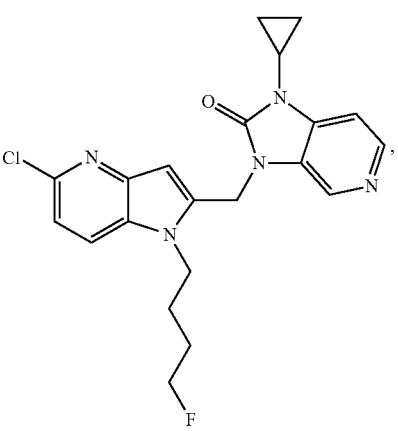

-continued
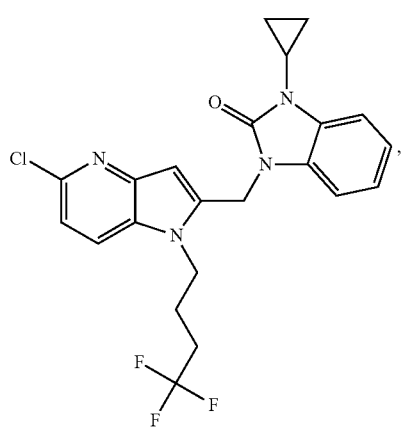
P43
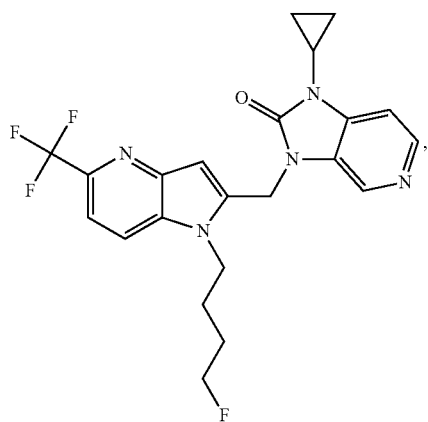
P46
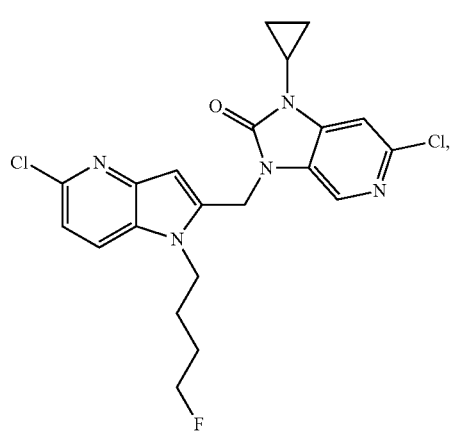
P44
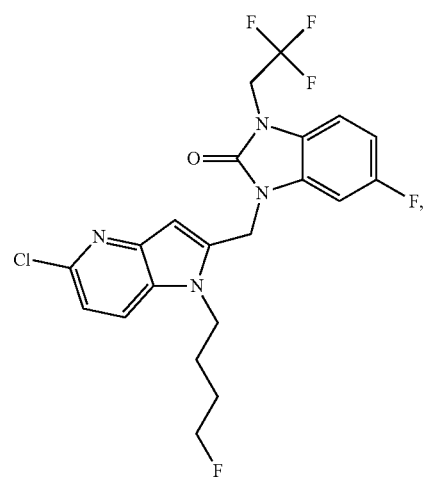
P47
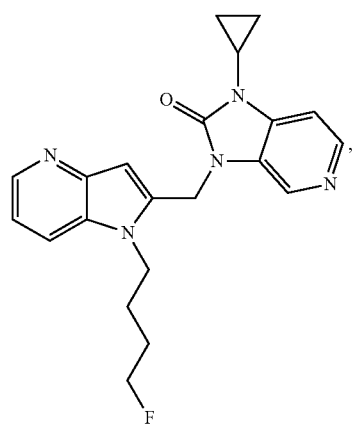
P45
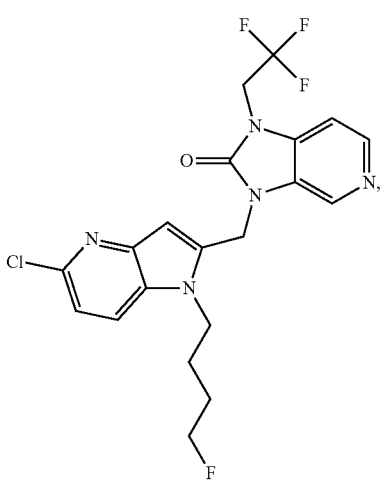
P48

P49 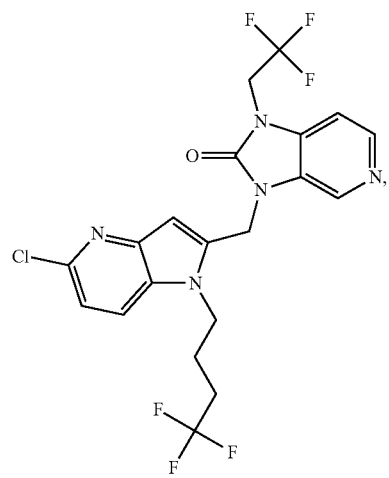
P50 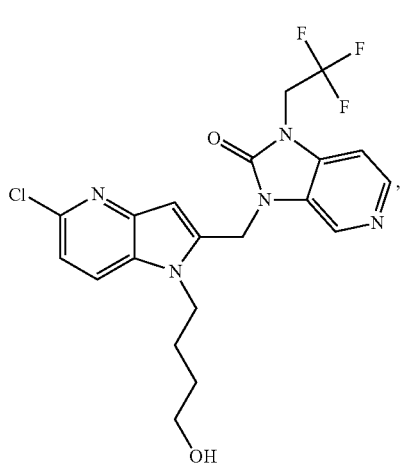
P51 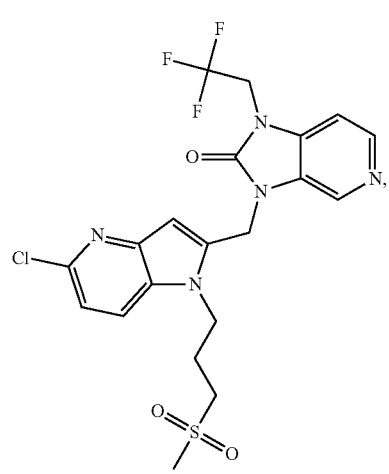
P52 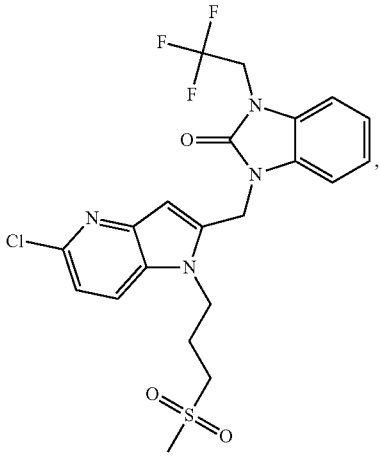
P53 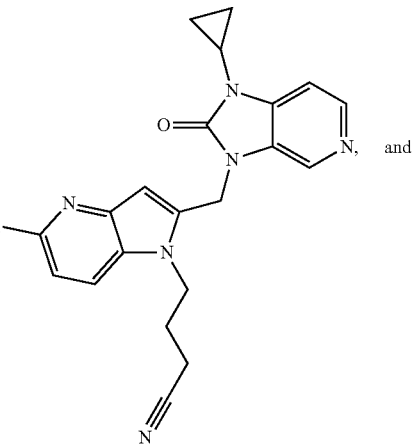
and
P54 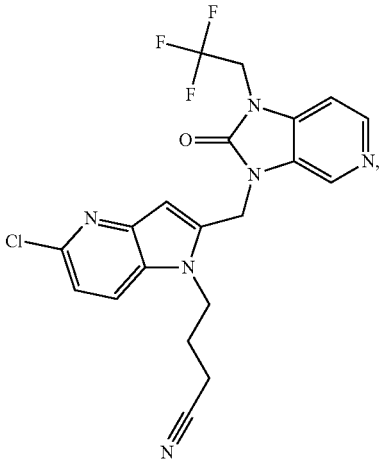
and an N-oxide, addition salt, or quaternary amine thereof.
* * * * *